(12) United States Patent
Pansky et al.

(10) Patent No.: US 11,478,234 B2
(45) Date of Patent: Oct. 25, 2022

(54) WORKING CHANNEL DEVICE FOR AN ENDOSCOPIC TOOL

(71) Applicant: T.A.G. Medical Products Corporation Ltd., Kibbutz Gaaton (IL)

(72) Inventors: Amir Pansky, Atlit (IL); Ben Zion Spector, Tel-Mond (IL)

(73) Assignee: T.A.G. Medical Products Corporation Ltd., Kibbutz Gaaton (IL)

( * ) Notice: Subject to any disclaimer, the term of this patent is extended or adjusted under 35 U.S.C. 154(b) by 0 days.

(21) Appl. No.: 16/362,971

(22) Filed: Mar. 25, 2019

(65) Prior Publication Data

US 2020/0315436 A1     Oct. 8, 2020

Related U.S. Application Data

(60) Provisional application No. 62/647,752, filed on Mar. 25, 2018.

(51) Int. Cl.
| | |
|---|---|
| *A61B 1/018* | (2006.01) |
| *A61B 1/005* | (2006.01) |
| *A61B 17/00* | (2006.01) |
| *A61B 17/32* | (2006.01) |

(52) U.S. Cl.
CPC ........... *A61B 17/00234* (2013.01); *A61B 17/320016* (2013.01); *A61B 2017/00292* (2013.01)

(58) Field of Classification Search
CPC . A61B 1/018; A61B 1/005; A61B 17/320016; A61B 17/00234; A61B 2017/00292; A61B 1/00087; A61B 1/045; A61B 1/0125; A61B 1/0051; A61B 1/0052; A61B 2017/320024; A61B 2017/00305; A61B 1/00101; A61B 1/00085; A61B 1/00098; A61B 1/0014; A61B 17/29; A61B 17/2909; A61B 2017/2927; A61B 2017/2905; A61B 2017/2908; A61B 17/32056

See application file for complete search history.

(56) References Cited

U.S. PATENT DOCUMENTS

| | | | |
|---|---|---|---|
| 7,678,117 B2 | 3/2010 | Hinman et al. | |
| 8,926,597 B2 * | 1/2015 | Lee | A61B 34/71 606/1 |
| 9,005,112 B2 | 4/2015 | Hasser et al. | |
| 10,245,029 B2 | 4/2019 | Hunter et al. | |

(Continued)

FOREIGN PATENT DOCUMENTS

WO    WO 2022/003659    1/2022

OTHER PUBLICATIONS

International Search Report and the Written Opinion dated Sep. 30, 2020 From the International Searching Authority Re. Application No. PCT/IL2020/05723. (8 Pages).

*Primary Examiner* — Anh T Dang

(57) ABSTRACT

An articulating working channel system for use with a plurality of flexible tools which are adapted to be interleaved in a single surgical procedure, comprising: a working channel subassembly including a hollow flexible shaft; and a surgical tool subassembly including the flexible tool, wherein the flexible tool includes a flexible tube which is adapted to be inserted into the flexible shaft and wherein the flexible shaft is adapted to be articulated and the flexible tube is adapted to be passively articulated therewith.

29 Claims, 34 Drawing Sheets

(56) References Cited

U.S. PATENT DOCUMENTS

| | | |
|---|---|---|
| 10,617,438 B2 | 4/2020 | O'Keefe et al. |
| 2008/0051802 A1* | 2/2008 | Schostek .............. A61B 1/3132 |
| | | 606/108 |
| 2008/0183035 A1* | 7/2008 | Vakharia .......... A61B 17/00234 |
| | | 600/104 |
| 2017/0065290 A1* | 3/2017 | Smith .............. A61B 17/32002 |
| 2021/0100576 A1 | 4/2021 | Pansky et al. |

* cited by examiner

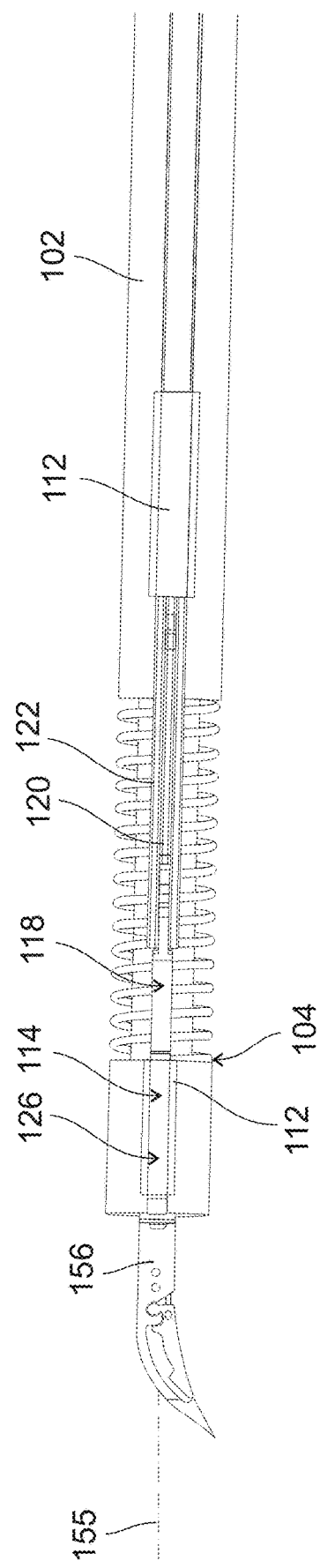

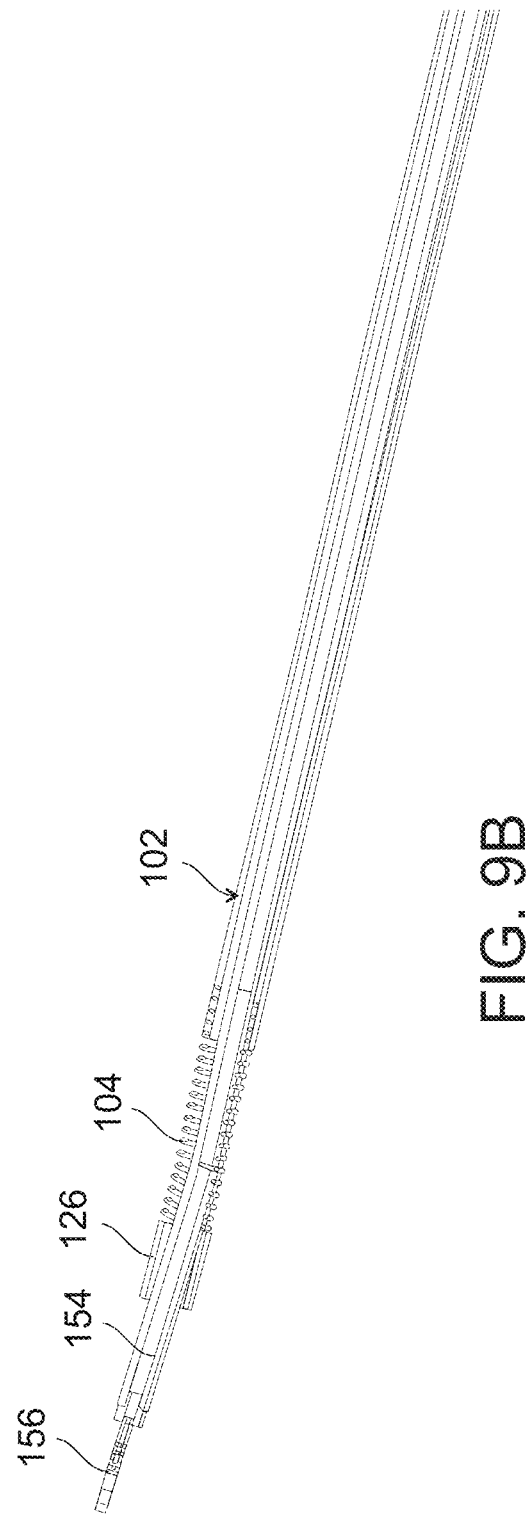

A

B

C

D

WORKING CHANNEL DEVICE FOR AN ENDOSCOPIC TOOL

RELATED APPLICATIONS

This application claims the benefit of priority under 35 USC § 119(e) of U.S. Provisional Patent Application No. 62/647,752 filed on Mar. 25, 2018, the contents of which are incorporated herein by reference as if fully set forth herein in their entirety.

This application is also related to U.S. Provisional Patent Application No. 62/279,817, filed on Jan. 17, 2016 and entitled "ARTICULATING DEVICE FOR USE IN ARTHROSCOPIC PROCEDURES," the disclosure of which is hereby incorporated by reference in its entirety.

FIELD AND BACKGROUND OF THE INVENTION

The present invention relates to a working channel device for use in endoscopic procedures and particularly in arthroscopic procedures.

Numerous surgical devices having a tool assembly for articulation are known in the art. Typically, such surgical devices include a fixed articulation which allows an operator to remotely access off-axis treatable regions.

Such articulating tool assemblies have become desirable, especially in the endoscopic surgical procedures. In an endoscopic surgical procedure, a distal end of the surgical device is inserted through small incisions into the body of a patient to access a surgical site. Typically, an appropriately sized cannula having a diameter of 4-7 mm is inserted through the incision to provide a guide channel for accessing the surgical site. It is desirable to provide small incisions to provide for less scarring, reduced trauma to the patient, faster healing time, thus the tolerances between the surgical device and the inner diameter of the cannula are small.

Conventional fixed articulating tool tips have a limited range due to the insertion cannula limited sizes. In order to be able to treat off-axis surgical site at relatively small angles of typically 45-110 degrees while inserted through the small diameter cannula, it is desirable to have a user controllable small articulating mechanism for surgical devices. Furthermore, in minimally invasive surgery in orthopedics, also known as arthroscopy, high stiffness of an invasive tool is required in order to be able to reach the surgical site in-between the bones while keeping the articulating tool at high resistive forces.

Various types of organs are involved in arthroscopic procedures such as solid bones, ligaments, condyles, muscles etc. Those organs span wide range of stiffness and therefore impose different demands on tools. For example, rigidity in order to allow reachability during maneuvering between bones for treatment. On the other hand, there is a need for controlled tools to handle soft tissues like ligaments. Thus, there is a need to provide a rigid tool to maneuver in between bones but then reaching off axis soft tissues in order to perform standard arthroscopy tasks such as cutting, wire manipulating, drilling, penetrating soft tissue in un-reachable or difficult to reach region.

Moreover, in many cases various tools are required to be exchanged during a single procedure. All tools are required to be used off-axis. For example, wire manipulation requires the use of suture passer, suture catcher and suture cutter.

SUMMARY OF THE INVENTION

There is thus provided, in accordance with some embodiments of the present invention, an articulating working channel system for use with a plurality of flexible tools which are adapted to be interleaved in a single surgical procedure, including a working channel subassembly including a hollow flexible shaft, a surgical tool subassembly including the flexible tool and wherein the flexible tool including a flexible tube which is adapted to be inserted into the flexible shaft and wherein the flexible shaft is adapted to be articulated and the flexible tube is adapted to be passively articulated therewith.

Preferably, the flexible tube is adapted to be axially displaced with respect to the flexible shaft. Additionally, the flexible tube is adapted to be rotationally displaced with respect to the flexible shaft.

In accordance with some embodiments of the present invention, the working channel subassembly and the surgical tool subassembly are adapted to be operated using a single handle.

BRIEF DESCRIPTION OF THE SEVERAL VIEWS OF THE DRAWINGS

The present invention will be understood and appreciated more fully from the following detailed description, taken in conjunction with the drawings in which:

FIG. 2A is a simplified first side enlargement view of a distal end of the working channel device of FIG. 1C;

FIG. 9B is a simplified sectional view of a distal end of the working channel device of FIG. 7;

DETAILED DESCRIPTION OF EMBODIMENTS OF INVENTION

In accordance with some embodiments of the present invention an articulating endoscopic tool is adapted to be inserted through an at least partially flexible hollow shaft. The endoscopic tool can be oriented at various rotational positions when required due to the articulation feature. It is a particular feature of an embodiment of the present invention that the hollow shaft is used as a working channel for various flexible tools in order to allow the user to reach the target region and introduce multiple surgical tools while staying at or near the target region.

In accordance with some embodiments of the present invention a re-usable spine is attached to the flexible hollow shaft, which is typically disposable. It is a particular feature of an embodiment of the present invention that the flexible hollow shaft is attached to the spine, enabling the hollow shaft to follow the articulation of the spine.

In some embodiments of the present invention the hollow shaft is generally expandable to allow non-regular endoscopic tools head insertion therethrough. In an alternative embodiment of the present invention, multiple disposable endoscopic tools can be repeatedly inserted through the hollow shaft.

In some embodiments of the present invention, a system and method of articulated working channel with plural flexible endoscopic tools, which can be interleaved in a single surgical procedure provides a cost effective solution. This is enabled by a single articulated working channel, which may be reusable or disposable, and a flexible endoscopic tool which is passively articulated while following the articulation of the working channel.

In some embodiments of the present invention, a single hand use is enabled while providing for various degrees of freedom required to operate the various endoscopic tools, such as for example axial movement, rotation or articulation of the endoscopic tool or the working channel as well providing for the endoscopic tool specific function.

In some embodiments of the present invention, the working channel is oversized with respect to the flexible endoscopic tool to allow insertion of flexible tools while slanted. In alternative embodiments of the present invention, a method is described in which the slanting angulation of the working channel is decreased at least temporarily in order to insert or redrawn the endoscopic flexible tool into and out of the working channel.

Figure 1A:
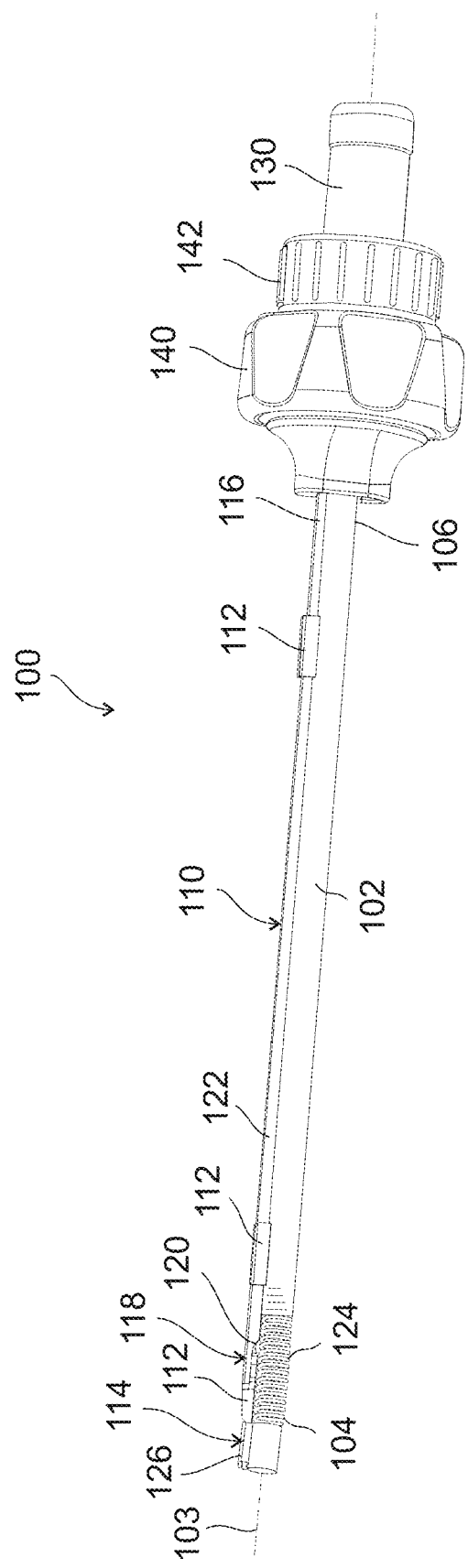
FIG. 1A is a simplified pictorial illustration of a working channel device sub-assembly, the working channel device shown in a first operative orientation and constructed and operative in accordance with an embodiment of the present invention.
Figure 1B:
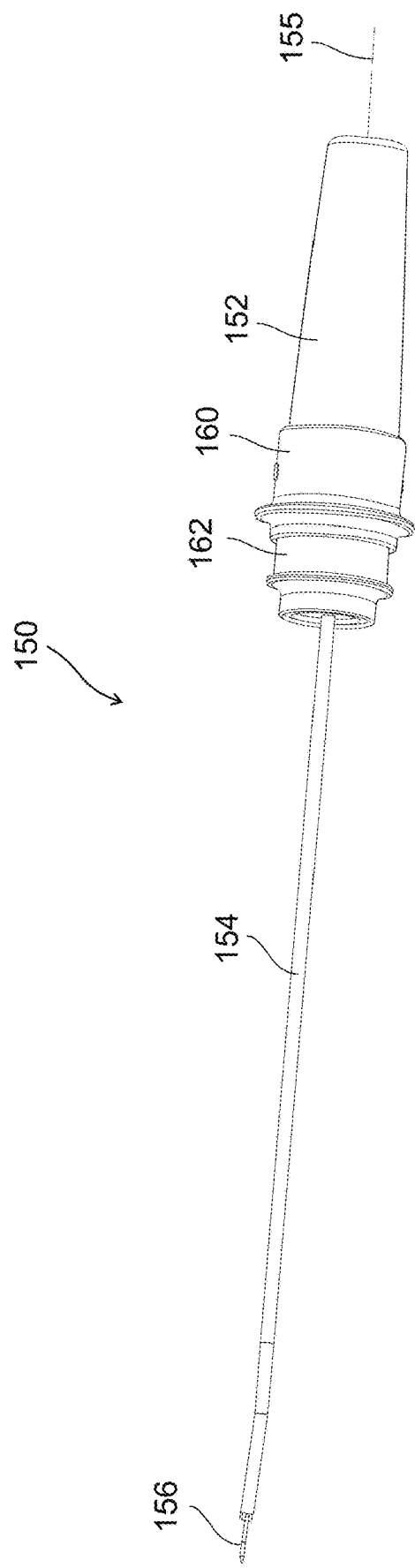
FIG. 1B is a simplified pictorial illustration of an endoscopic tool sub-assembly, the endoscopic tool shown in a first operative orientation and constructed and operative in accordance with an embodiment of the present invention.
Figure 1C:
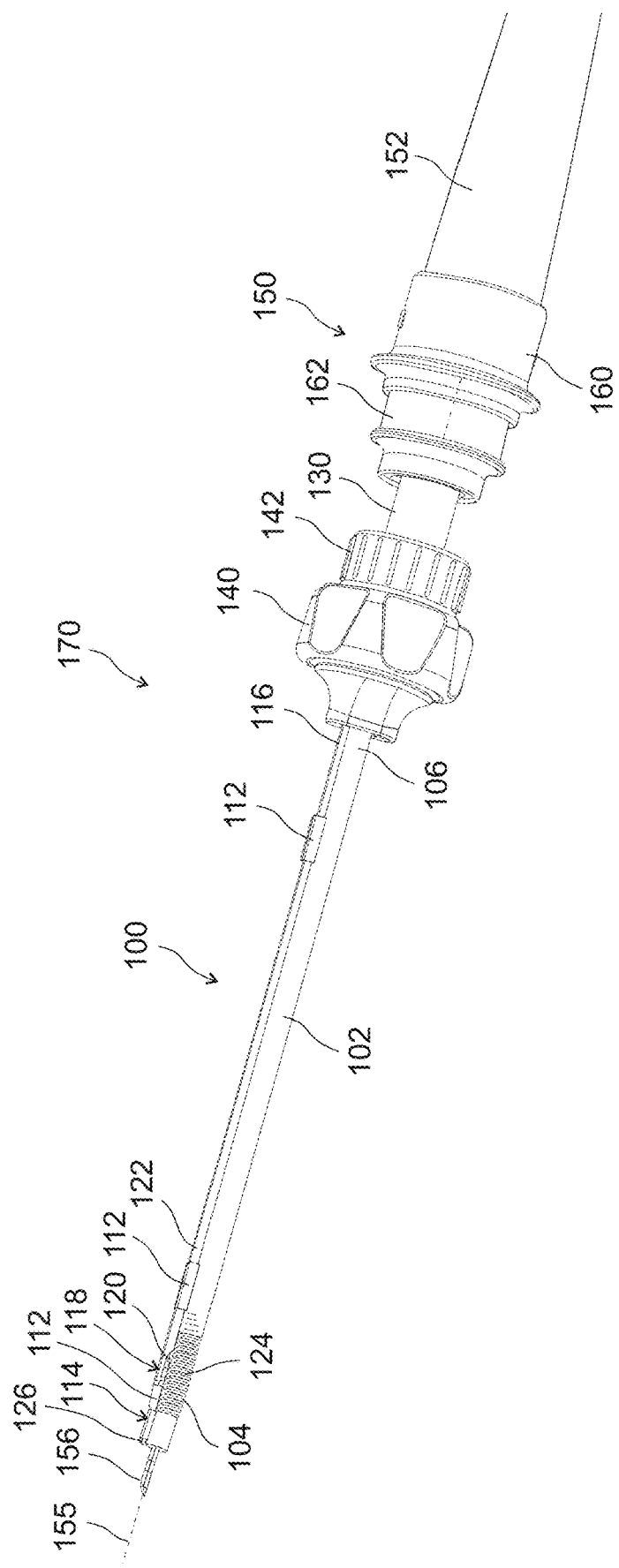
FIG. 1C is a simplified pictorial illustration of an assembled working channel device having an endoscopic tool inserted therethrough, the working channel device is shown in a first operative orientation and is constructed and operative in accordance with an embodiment of the present invention.

Reference is now made to FIG. 1A, which is a simplified pictorial illustration of a working channel device sub-assembly, the working channel device is shown in a first operative orientation and is constructed and operative in accordance with an embodiment of the present invention and to FIG. 1B, which is a simplified pictorial illustration of an endoscopic tool sub-assembly, the endoscopic tool is shown in a first operative orientation and is constructed and operative in accordance with an embodiment of the present invention and to FIG. 1C, which is a simplified pictorial illustration of an assembled working channel device having an endoscopic tool inserted therethrough, the working channel device is shown in a first operative orientation and is constructed and operative in accordance with an embodiment of the present invention.

Figure 2B:
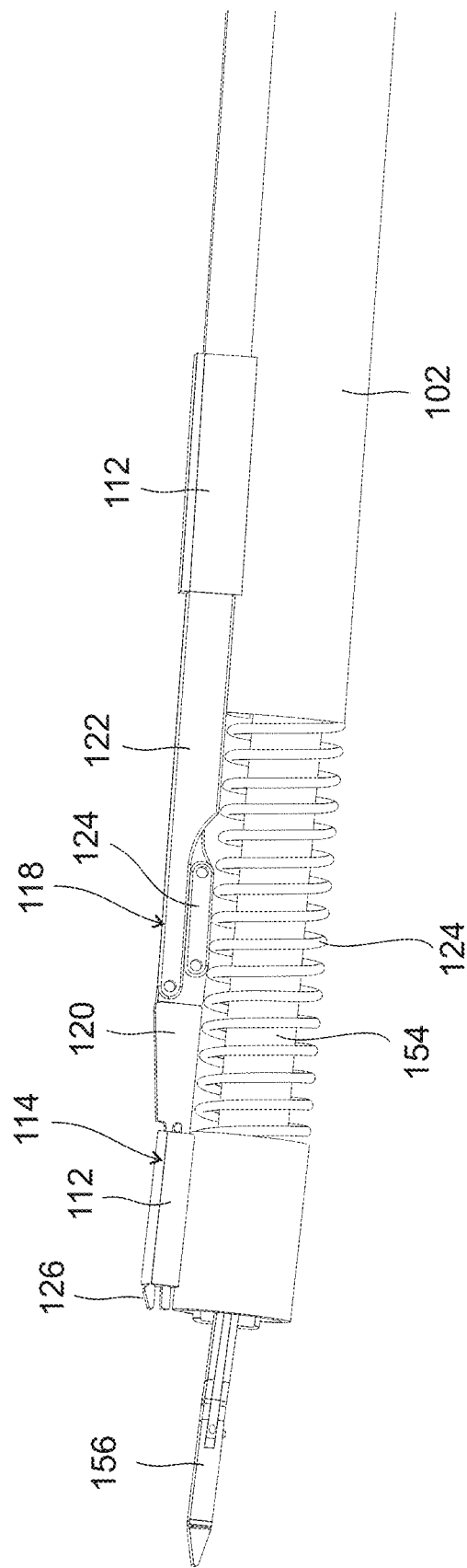
FIG. 2B is a simplified second side enlargement view of a distal end of the working channel device of FIG. 1C.

Reference is additionally made to FIG. 2A, which is a simplified first side enlargement view of a distal end of the working channel device of FIG. 1C and to FIG. 2B, which is a simplified second side enlargement view of a distal end of the working channel device of FIG. 1C.

Reference is now particularly made to FIG. 1A. A working channel device sub-assembly 100 is seen in FIG. 1A. The working channel device sub-assembly 100 preferably includes a longitudinal hollow shaft 102 extending along longitudinal axis 103, preferably made of a flexible material. The hollow shaft 102 has a distal portion 104 and a proximal portion 106. It is appreciated that at least the distal portion 104 is made of a flexible material. Alternatively, the hollow shaft 102 is made of a flexible material along its entire length. Preferably, the flexible region of the hollow shaft 102 is expandable.

It is noted that the hollow shaft may be made of metal, polymer, reinforced spring, braid, low durometer tube, PVC, coiled spring, spiral cross section tube, spiral tube or any other material that provides radial reinforcement.

Alternatively, only the distal portion 104 of hollow shaft 102 may be made of a coil spring or a flexible element.

In an alternative embodiment of the present invention, the hollow shaft 102 can be continuous or constructed from discrete elements, each of which may have different material or construction properties. For example, hollow shaft 102 may be either tubular or partially opened along its circumference. It is also appreciated that hollow shaft 102 can have various alternative cross-sections to accommodate various flexible tools.

Figure 16:
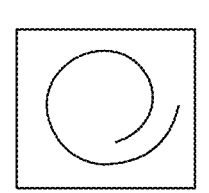
FIGS. 16A-D is a simplified illustration of various working channel construction embodiments.
Figure 16:
Figure 16:
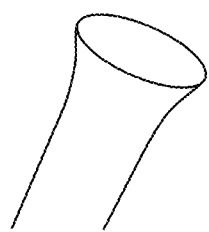
Figure 16:
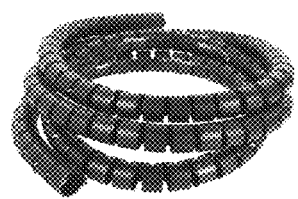

Various embodiments of hollow shaft 102 construction are shown in FIG. 16.

It is seen that in an embodiment A shown in FIG. 16, the hollow shaft 102 is made of a spiral open tube. Alternatively, in embodiment B shown in FIG. 16, the hollow shaft 102 is made of two rigid half tubes connected by a plurality of flexible strings. In an embodiment C, braided tube is shown. In an embodiment D, flexible tube composed of discrete elements is shown.

Figure 17:
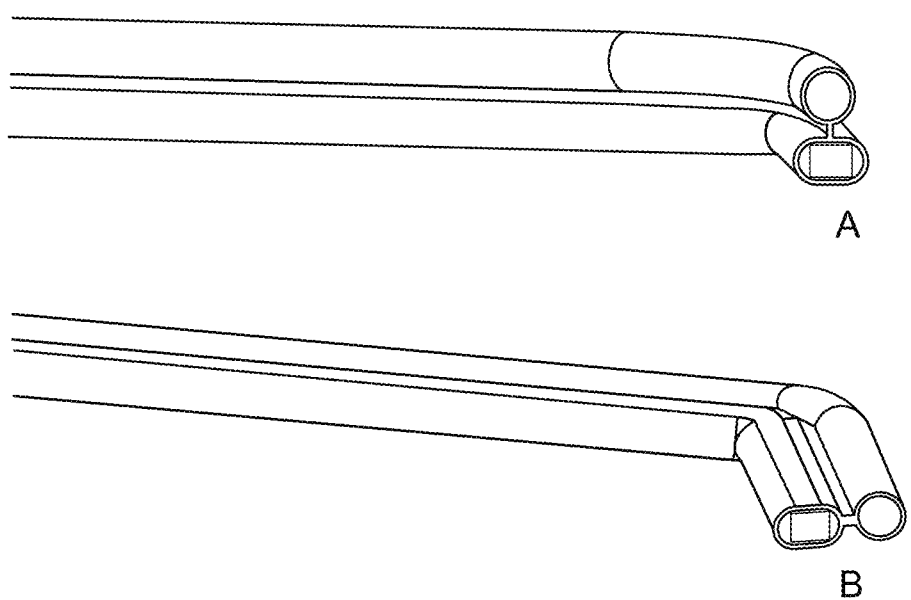
FIGS. 17A-B is a simplified pictorial illustration of various working channel profiles.

Various working channel profiles are shown in FIG. 17. In an embodiment A, high profile of working channel is shown. In an embodiment B, low profile of working channel is shown, which may be suitable for small surgical areas.

Figure 18:
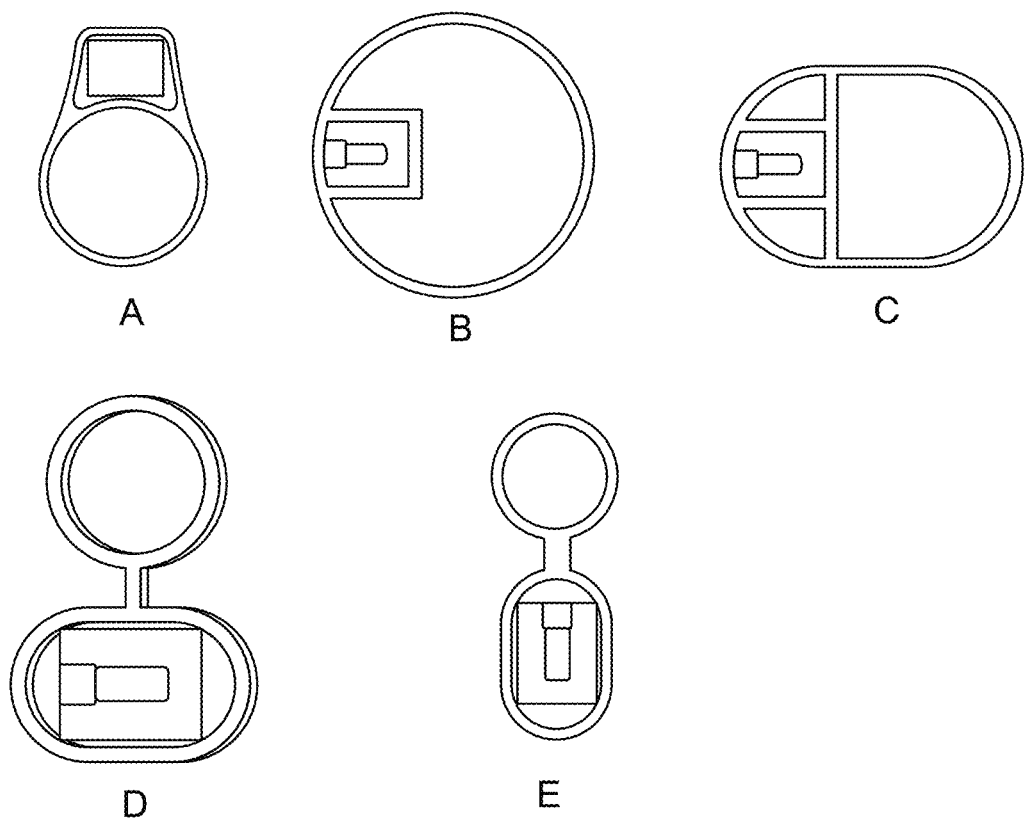
FIGS. 18A-E is a simplified cross-section view illustration of various working channel profiles.

Various cross-sectional view illustrations of working channels are shown in FIG. 18, embodiments A-E.

It is further seen in FIG. 1A that a relatively rigid spine 110 is longitudinally attached along the length of hollow shaft 102, typically by means of snapping elements 112 or any other suitable attachment means. It is appreciated that spine 110 has a distal end 114 and a proximal end 116. An articulating joint 118 is typically positioned adjacent to distal end 114 of spine 110.

It is appreciated that the spine 110 is preferably rigid along the majority of its longitudinal extent and extends in parallel to longitudinal axis 103, but it is pivotable at the articulating joint 118.

In this particular embodiment of the present invention the spine 110 includes a spine push rod 120, which is enclosed within a spine cover 122. The spine push rod 120 is hingedly attached to a connector 124, which is in turn hingedly connected to a distal end 126, which is typically locked to the distal portion 104 of hollow shaft 102. It is noted that spine cover 122 is configured to protect the tissue while inserting the working channel device sub-assembly 100 into the body of the patient. Alternatively, the spine 110 can be positioned within the hollow shaft 102 or it can be provided with no spine cover 122.

It is noted that any kind of hinge mechanism may be provided in order to articulate the distal end 114 of spine 110 and as a result bending the distal portion 104 of hollow shaft 102.

It is appreciated that in alternative embodiments of the present invention, the spine 110 is loosely attached to the hollow shaft 102, thus obviating the need for the hollow shaft 102 to follow the trajectory of spine 110. The hollow shaft 102 may be partially floating and not attached to spine 110 and may be only attached to spine 110 at its distal end.

It is further appreciated that the spine 110 can be blunt or it can perform a certain surgical function, such as grasping or passing surgical sutures for example.

It is a particular feature of an embodiment of the present invention that the hollow shaft 102 is configured for insertion of various endoscopic tools therethrough. Spine 110 is attached to hollow shaft 102 in order to provide rigidity to the hollow shaft 102 and enable navigation of the working channel device sub-assembly 100 through the tissue. The articulating joint 118 of spine 110 urges the distal portion 114 to bend and provide for articulation of the endoscopic tool therewithin.

A working channel handgrip 130 extends proximally from the proximal portion 106 of the hollow shaft 102 and is arranged coaxially therewith. In other embodiment, the hollow shaft 102 and the working channel handgrip 130 can be snapped horizontally.

A working channel articulating knob 140 is provided adjacent the proximal portion of hollow shaft 106 and is adapted due to rotation thereof for articulating spine 110 as will be described in detail hereinbelow.

It is additionally seen in FIG. 1A that a locking knob 142 is provided proximally and adjacent to articulating knob 140 and adapted to lock the spine 110 in a particular articulation angle, as will be described in detail hereinbelow.

It is a particular feature of an embodiment of the present invention that part of the working channel subassembly 100, such as the spine 110 may be reusable and part of the working channel subassembly 100, such as the hollow shaft 102 may be disposable.

Reference is now particularly made to FIG. 1B. An endoscopic tool sub-assembly 150 preferably includes a tool handgrip 152 and a flexible shaft 154 extending distally therefrom and arranged along longitudinal axis 155. An endoscopic tool 156, such as for example a needle, a suture passer, grasper or cutter is typically fixedly attached to the distal end of flexible shaft 154.

Alternatively, the flexible shaft 154 may be only partially flexible at its distal end and rigid along the remaining length of the shaft 154. For example, the shaft 154 can be flexible only along the longitudinal extent which is adapted to extend distally out of the hollow shaft 102.

It is a particular feature of an embodiment of the present invention that substantially long rigid endoscopic tool 156 mounted onto flexible shaft 154 can be accommodated by flexible shaft 102 due to the fact that the hollow shaft 102 is extendable during use and returns to its initial orientation after use.

An activating knob 160 is provided on the tool handgrip 152 and due to its axial displacement along axis 155, activates the endoscopic tool 156, as will be described in detail hereinbelow. This activation preferably includes opening of the needle, grasper, passer using a flexible wire mechanism such as previously disclosed in patent application U.S. patent 62/279,817, the disclosure of which is hereby incorporated by reference in its entirety. A locking knob 162 is positioned distally from and adjacent to activating knob 160 and adapted for locking the endoscopic tool 156 axially with respect to the working channel subassembly 100 at a desired axial location.

Reference is now particularly made to FIG. 1C. An assembled working channel device 170 having an endoscopic tool inserted therethrough is seen in FIG. 1C.

It is a particular feature of an embodiment of the present invention that the endoscopic tool subassembly 150 is slidably inserted into the working channel subassembly 100 to form a single working channel device 170 with a single multi-functional handle enabling various axial and rotational movements of the endoscopic tool 156 within the body of a patient.

The endoscopic tool subassembly 150 is slidably received into working channel subassembly 100 and both are arranged along a single longitudinal axis, axis 103 and axis 155, which are aligned.

The working channel device 170 is shown in a first operative orientation in FIGS. 1C, 2A & 2B. In this first operative orientation, the following spatial relations exist:

The endoscopic tool 156 is shown in an un-activated closed orientation, as particularly seen in FIG. 2A.

The endoscopic tool 156 is positioned in its retracted orientation with respect to hollow shaft 102, such that flexible shaft 154 is substantially enclosed within hollow shaft 102 and only the endoscopic tool 156 protrudes distally therefrom. This retracted orientation of the endoscopic tool 156 results from the fact that the locking knob 162 is proximally spaced from locking knob 142. The endoscopic tool 156 may extend out of the hollow shaft 102 as far as 12 mm, for example.

It is further seen that in an embodiment of the present invention, in this first operative orientation, the endoscopic tool 156 extends along a plane which is disposed transversely to the plane along which spine 110 extends. It is appreciated that alternatively, the endoscopic tool 156 can be initially oriented at any other angle of rotation about its longitudinal axis.

It is a particular feature of an embodiment of the present invention that the endoscopic tool subassembly 150 has various degrees of freedom within the working channel sub-assembly 100, such as rotation of the endoscopic tool subassembly 150 about its axis, axial relative movement of the endoscopic tool subassembly 150 relative to the working channel subassembly 100 and activation of the endoscopic tool 156 while the endoscopic tool subassembly 150 is mounted within the working channel subassembly 100.

The working channel subassembly 100 is positioned in a non-bent orientation in FIGS. 1A, 2A & 2B due to the fact that the working channel articulating knob 140 is in a first non-activated orientation.

It is a particular feature of an embodiment of the present invention that the flexible shaft 154 of the endoscopic tool subassembly 150 follows the geometry of the hollow shaft 102, whereas spine 110 provides the required rigidity to the hollow shaft 102 and as a consequence to flexible shaft 154. Once the spine 110 is bent, the hollow shaft 102 is bent with it, since the hollow shaft 102 is locked to the spine 110 and in turn the flexible shaft 154 is bent as well and enables articulation of the endoscopic tool 156 with respect to longitudinal axis 155.

Figure 3A:
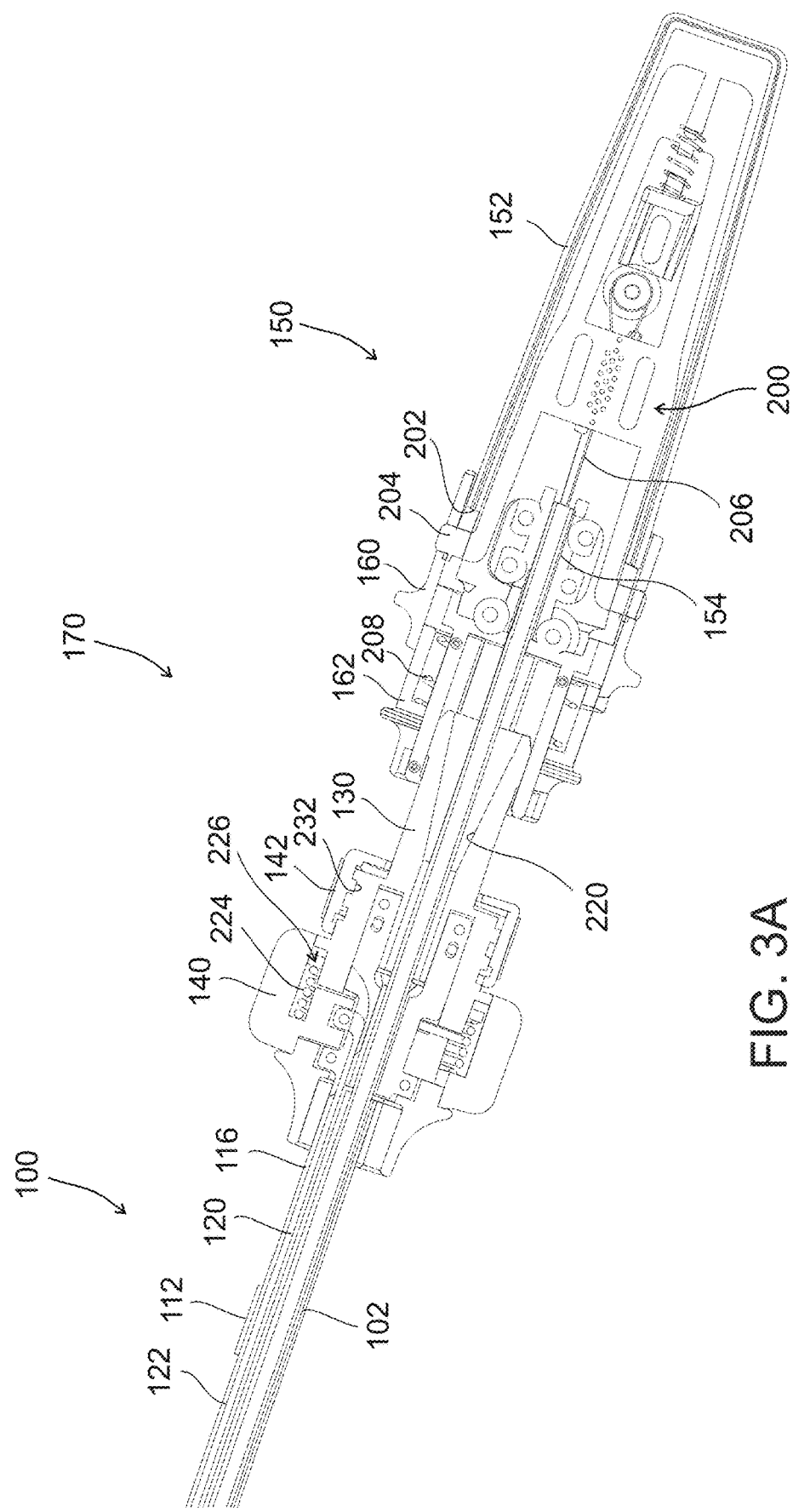
FIG. 3A is a simplified sectional view of the handle containing an operating mechanism of the working channel device of FIG. 1C.
Figure 3B:
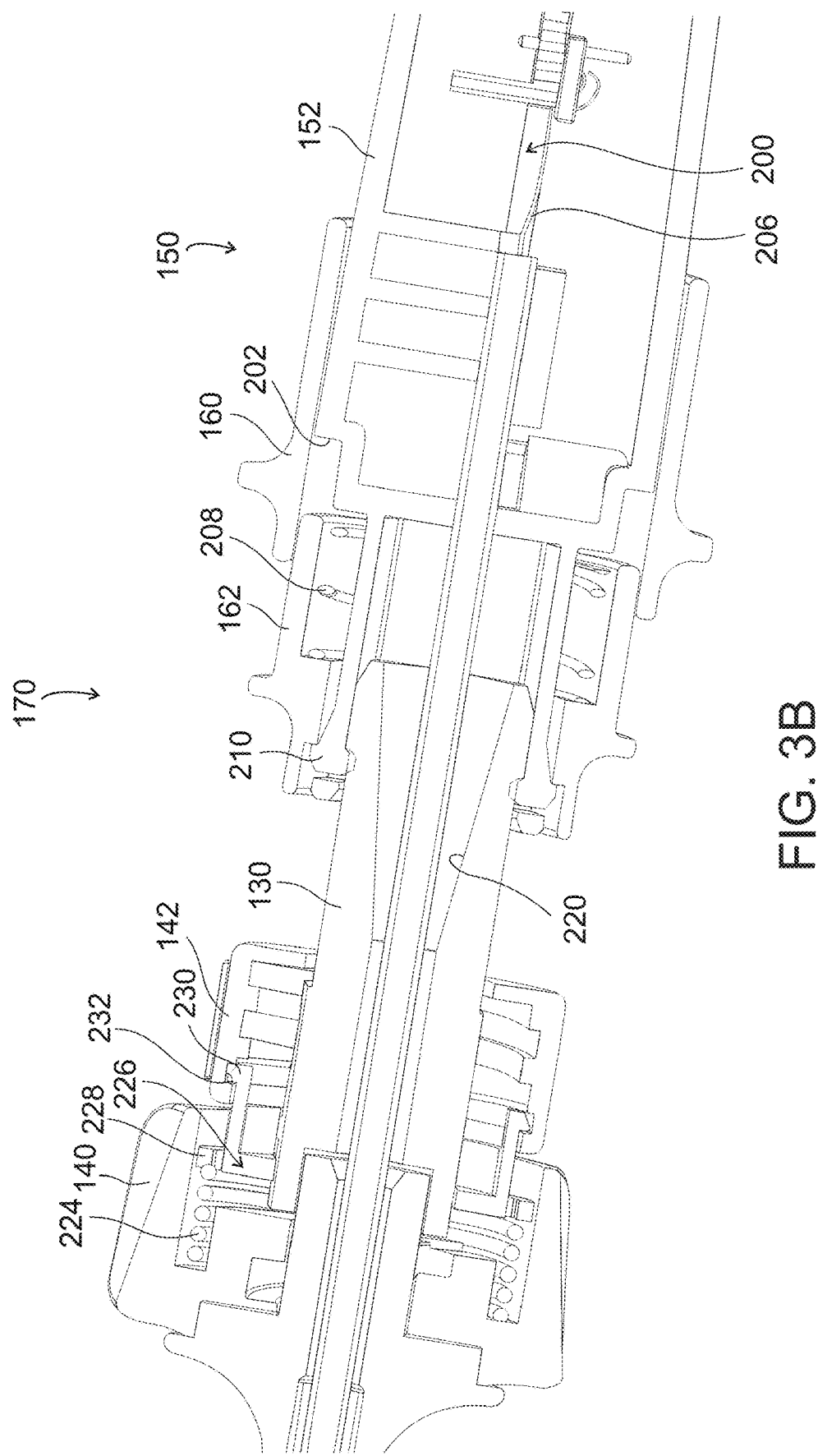
FIG. 3B is a simplified enlarged section view of FIG. 3A.
Figure 3C:
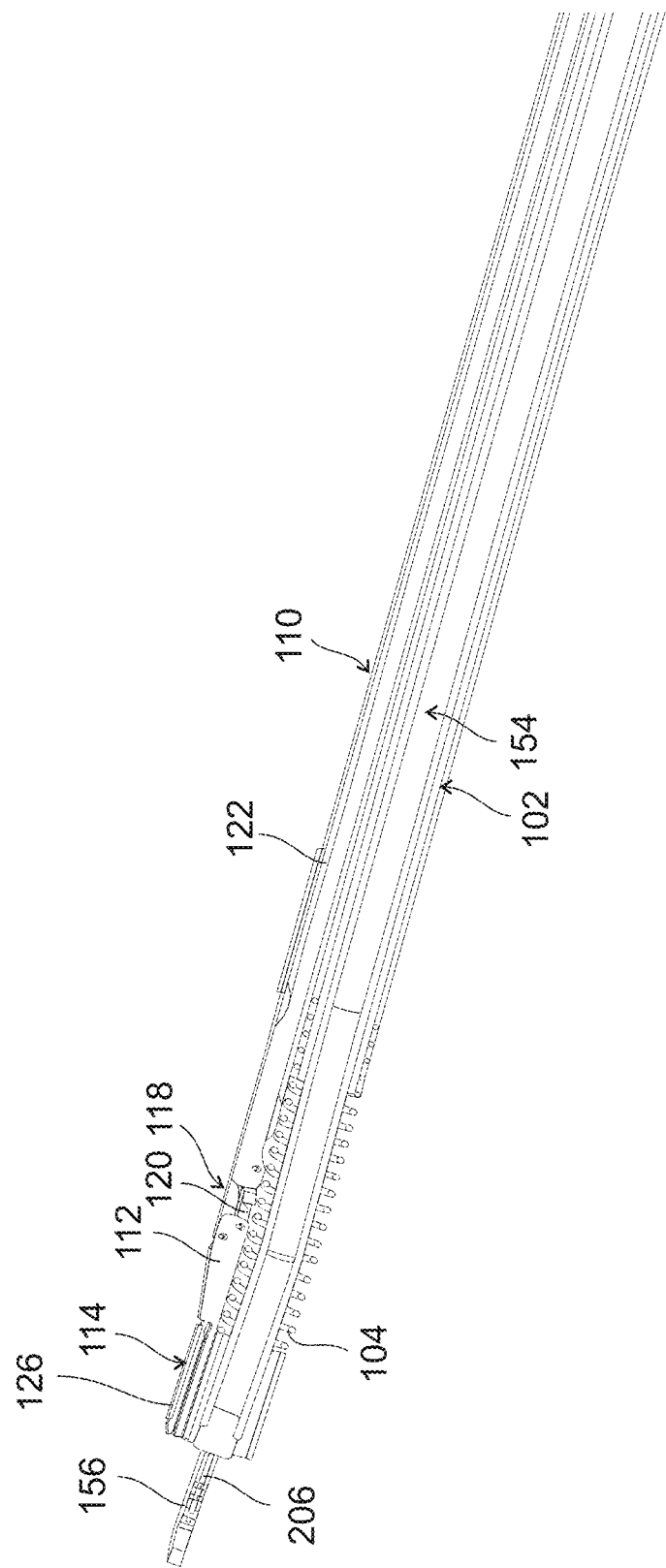
FIG. 3C is a simplified sectional view of a distal end of the working channel device of FIG. 1C.

Reference is now made to FIG. 3A, which is a simplified sectional view of the handle containing an operating mechanism of the working channel device 170 of FIG. 1C, FIG. 3B, which is a simplified enlarged sectional view of FIG. 3A and to FIG. 3B, which is a simplified sectional view of a distal end of the working channel device 170 of FIG. 1C.

It is seen in FIG. 3A that endoscopic tool activation mechanism 200 is typically enclosed within tool handgrip 152 and is preferably fixedly attached to activating knob 160. It is also seen that a longitudinal opening 202 is formed on each side of the tool handgrip 152. An outwardly extending protrusion 204 of the endoscopic tool activation mechanism 200 extends through each of openings 202 and protrusions 204 are slidable within openings 202 once activating knob 160 is axially displaced.

Flexible shaft 154 is preferably fixedly retained within handgrip 152. A flexible wire mechanism 206 is attached at one side to the endoscopic tool 156 and at another side to the endoscopic tool activation mechanism 200.

It is appreciated that when the activating knob 160 is positioned at its distal position, protrusions 204 are located typically at the distal end of openings 202, in this position the flexible wire mechanism 206 is not activated and the endoscopic tool 156 is closed. Once the activating knob 160 is displaced axially proximally to its proximal position, it displaces the protrusions 204 proximally along openings 202 due to fixed attachment of the endoscopic tool activation mechanism 200 and the activating knob 160, thus activating the flexible wire mechanism 206 and consequently activating the endoscopic tool 156, such as for example opening the needle.

It is further particularly seen in FIGS. 3A & 3B that locking button 162, which is disposed distally to activating knob 160 is adapted to lock the endoscopic tool 156 axially with respect to the working channel subassembly 100 at a desired axial location. Locking button 162 enables locking of the endoscopic tool 156 with respect to working channel subassembly 100 by means of a spring 208, which biases the locking button 162 distally, thus the inner surface of locking button 162 applies radial force on and inwardly deflects deformable leaves 210 formed on the outer surface of the distal end of tool handgrip 152 of the endoscopic tool sub-assembly 150. This engagement between the locking button 162 and deformable leaves 210 results in increased friction between handgrip 130 and endoscopic tool subassembly 150, thus axially locking the endoscopic tool 156 with respect to the working channel subassembly 100.

It is further seen in FIG. 3A that handgrip 130 of the work channel subassembly 100 defines an outwardly conical lumen 220 for insertion of the flexible shaft 154 therein and further into the hollow shaft 102.

It is additionally seen in FIG. 3A that the hollow shaft 102 is fixedly attached to handgrip 130 of the working shaft subassembly 100. The spine cover 122 is also fixedly attached to handgrip 130 and spine pushrod 120 is fixedly attached to working channel articulating knob 140, having an inner helical groove path 222 (shown further in FIGS. 12B & 15B), so that upon rotation of working channel articulating knob 140, the spine pushrod 120 is axially distally displaced due to displacement along inner helical groove path 222. Axial displacement of spine pushrod 120 causes bending articulating joint 118, and thus bending of hollow shaft 102, and in turn bending of flexible shaft 154 of the endoscopic tool subassembly 150.

It is further seen in FIGS. 3A-B that a coil spring 224 is disposed within working channel articulating knob 140 and the spring 224 is supported at its distal end on the inner proximally facing surface of working channel articulating knob 140 and at its proximal end on a locking element 226. The locking element 226, as particularly shown in FIG. 12C, includes a disc element 228 and proximally spaced outwardly extending snap engagement ears 230 which are engaged with an inner threading 232 of locking knob 142.

It is appreciated that each bending angle of the articulating joint 118, and as a consequence of the hollow shaft 102 and flexible shaft 154 can be temporarily locked by means of rotation of locking knob 142, which locks further rotation of working channel articulating knob 140. The working channel articulating knob 140 is biased to the proximal orientation of spine pushrod 120, in which the articulating joint 118 is non-bent, by means of the biasing force of spring 224.

It is particularly seen in FIG. 3B that the articulating joint 118 is in its non-bent orientation and thus flexible shaft 154 is not bent and endoscopic tool 156 extends substantially along longitudinal axis 155. Additionally, preferably only the endoscopic tool 156 extends from hollow shaft 102 of the working channel subassembly 100, whereas the flexible shaft 154 is enclosed within the hollow shaft 102 in this first operative orientation.

It is a particular feature of an embodiment of the present invention that the working channel device has various degrees of freedom, such that the endoscopic tool subassembly 150 can be manually rotated with respect to the working channel subassembly 100. The entire working channel assembly 170 can be manually rotated within the patient body in order to introduce the endoscopic tool 156 at a different orientation.

It is appreciated that the articulating joint 118 can be initially positioned at a non-bent orientation and bending of the articulating joint at angles of 0-90° with respect to longitudinal axis 155 is enabled by working channel articulating knob 140. Alternatively, the articulating joint 118 can be initially positioned at angle with respect to longitudinal axis 155, such as −45° and then bending of the articulation joint 118 up to an angle of +45° with respect to longitudinal axis 155 is enabled by working channel articulating knob 140.

It is further appreciated that various endoscopic tools may be repeatedly interchanged within the working channel subassembly 100 during a single procedure. It is appreciated that various tools can be used, such as tools useful for arthroscopy, laparoscopy and other medical applications.

Figure 4:
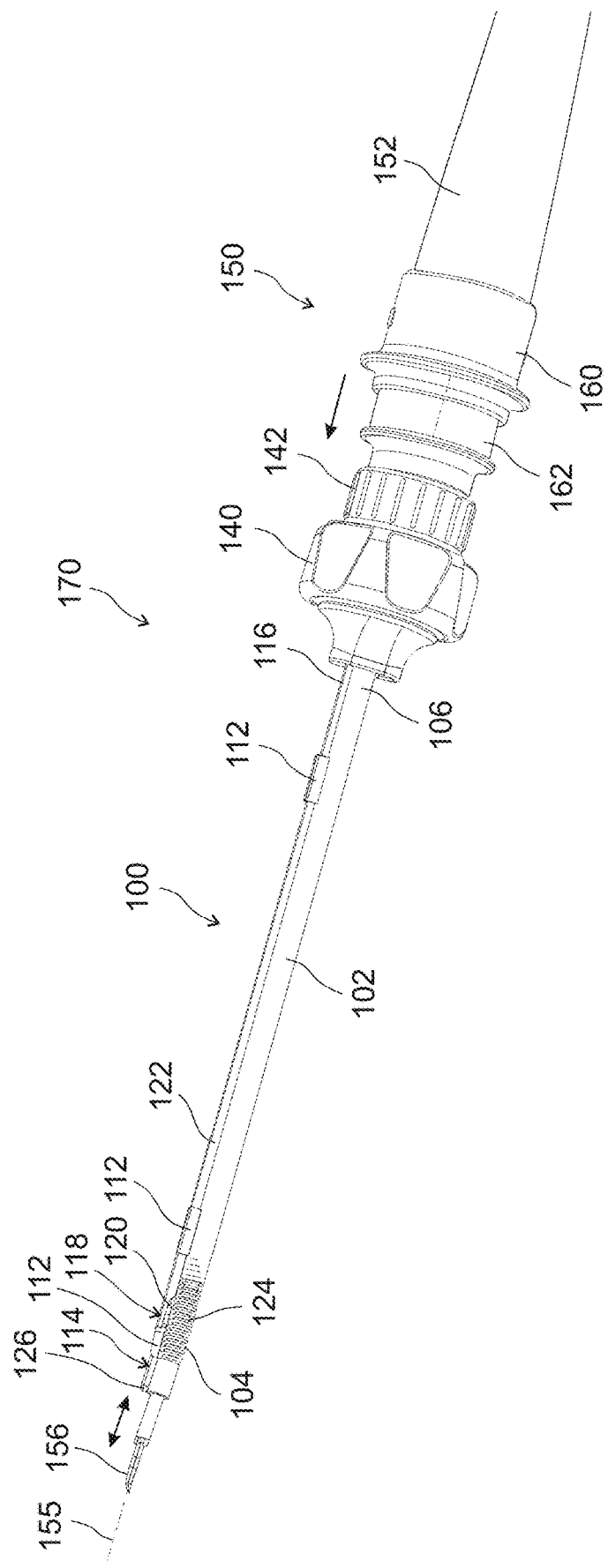
FIG. 4 is a simplified pictorial illustration of a working channel device having an endoscopic tool inserted therethrough, the working channel device is shown in a second operative orientation and is constructed and operative in accordance with an embodiment of the present invention.
Figure 5A:
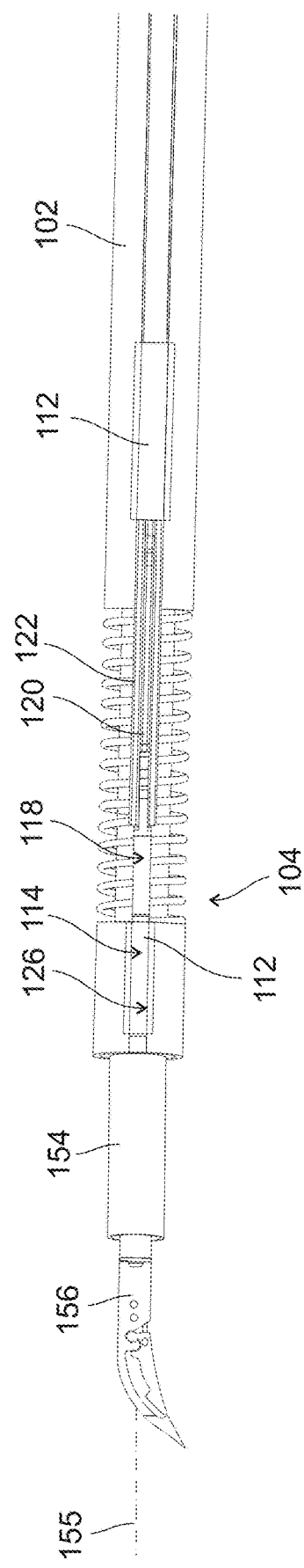
FIG. 5A is a simplified first side enlargement view of a distal end of the working channel device of FIG. 4.

Reference is now made to FIG. 4, which is a simplified pictorial illustration of a working channel device having an endoscopic tool inserted therethrough, the working channel device is shown in a second operative orientation and is constructed and operative in accordance with an embodiment of the present invention. Reference is additionally made to FIG. 5A, which is a simplified first side enlargement view of a distal end of the working channel device of FIG. 4 and to FIG. 5B, which is a simplified second side enlargement view of a distal end of the working channel device of FIG. 4.

An assembled working channel device 170 having an endoscopic tool inserted therethrough is seen in FIG. 4.

It is a particular feature of an embodiment of the present invention that the endoscopic tool subassembly 150 is slidably inserted into the working channel subassembly 100 to form a single working channel device 170 with a single multi-functional handle enabling various axial and rotational movements of the endoscopic tool 156 within the body of a patient.

The endoscopic tool subassembly 150 is slidably received into working channel subassembly 100 and both are arranged along a single longitudinal axis, axis 103 and axis 155, which are aligned.

Figure 5B:
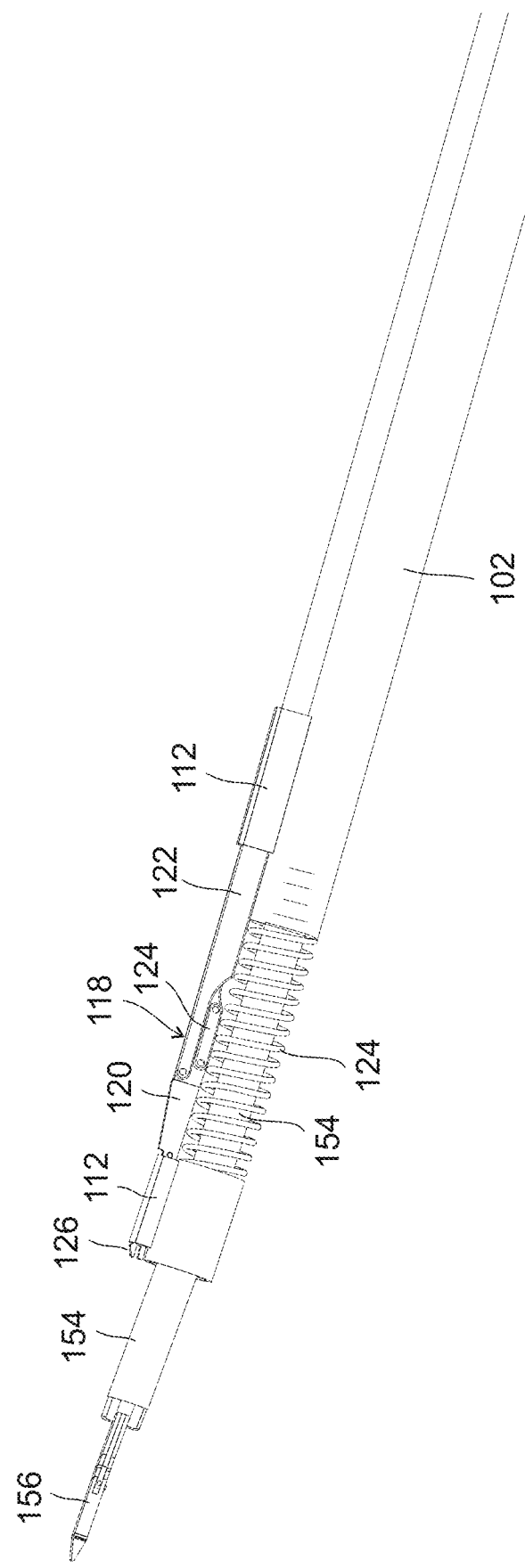
FIG. 5B is a simplified second side enlargement view of a distal end of the working channel device of FIG. 4.

The working channel device 170 is shown in a second operative orientation in FIGS. 4, 5A & 5B. In this second operative orientation, the following spatial relations exist: The endoscopic tool 156 is shown in an un-activated closed orientation, as particularly seen in FIG. 5A.

The endoscopic tool 156 is positioned in its extended orientation with respect to hollow shaft 102, such that flexible shaft 154 partially protrudes distally from hollow shaft 102 and the endoscopic tool 156 is spaced distally from the distal end of the hollow shaft 102. This extended orientation of the endoscopic tool 156 results from the fact that the endoscopic tool subassembly 150 is displaced distally with respect to working channel subassembly 100 such that the locking knob 162 now abuts locking knob 142. The endoscopic tool 156 may extend out of the hollow shaft 102 as far as 12 mm, for example.

It is further seen that in an embodiment of the present invention, in this second operative orientation, the endoscopic tool 156 extends along a plane which is disposed transversely to the plane along which spine 110 extends. It is appreciated that alternatively, the endoscopic tool 156 can be initially oriented at any other angle of rotation about its longitudinal axis.

It is a particular feature of an embodiment of the present invention that the endoscopic tool subassembly 150 has various degrees of freedom within the working channel sub-assembly 100, such as rotation of the endoscopic tool subassembly 150 about its axis, axial relative movement of the endoscopic tool subassembly 150 relative to the working channel subassembly 100 and activation of the endoscopic tool 156 while the endoscopic tool subassembly 150 is mounted within the working channel subassembly 100.

The working channel subassembly 100 is positioned in a non-bent orientation in FIGS. 4, 5A & 5B due to the fact that the working channel articulating knob 140 is in a first non-activated orientation.

It is a particular feature of an embodiment of the present invention that the flexible shaft 154 of the endoscopic tool subassembly 150 follows the geometry of the hollow shaft 102, whereas spine 110 provides the required rigidity to the hollow shaft 102 and as a consequence to flexible shaft 154. Once the spine 110 is bent, the hollow shaft 102 is bent with it, since the hollow shaft 102 is locked to the spine 110 and in turn the flexible shaft 154 is bent as well and enables articulation of the endoscopic tool 156 with respect to longitudinal axis 155.

Figure 6A:
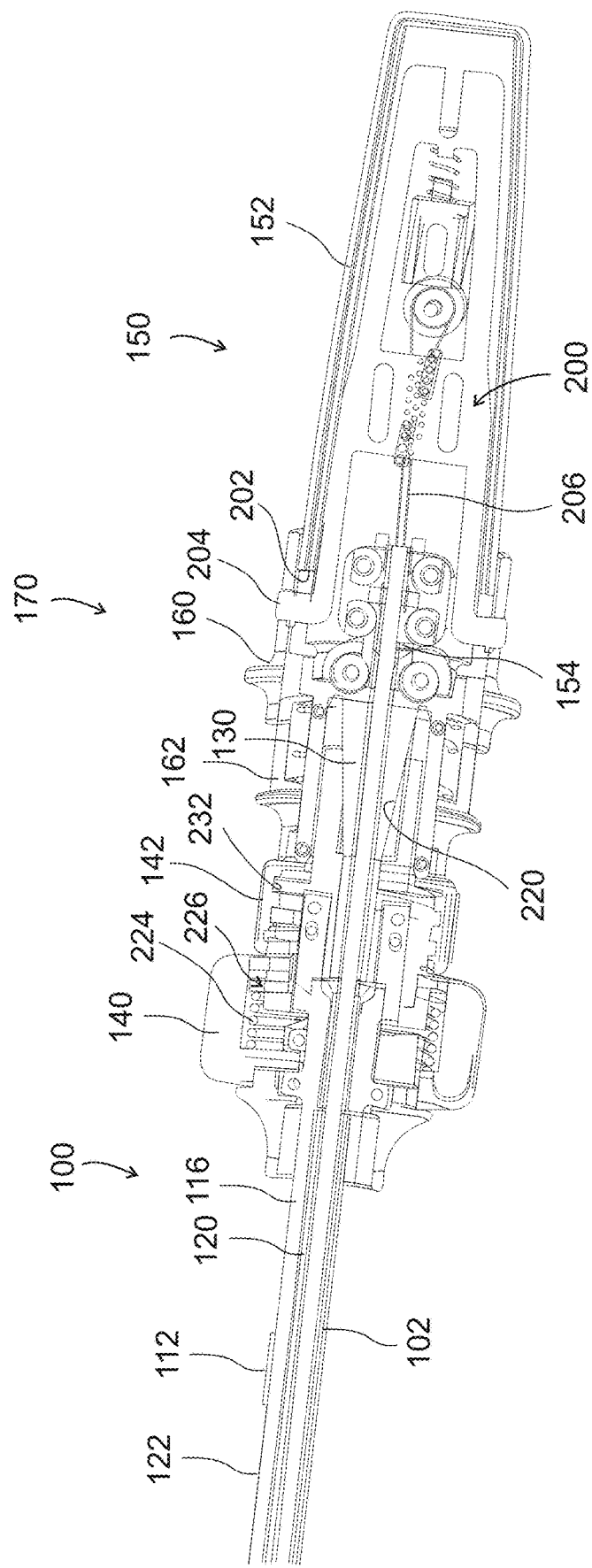
FIG. 6A is a simplified sectional view of the handle containing an operating mechanism of the working channel device of FIG. 4.
Figure 6B:
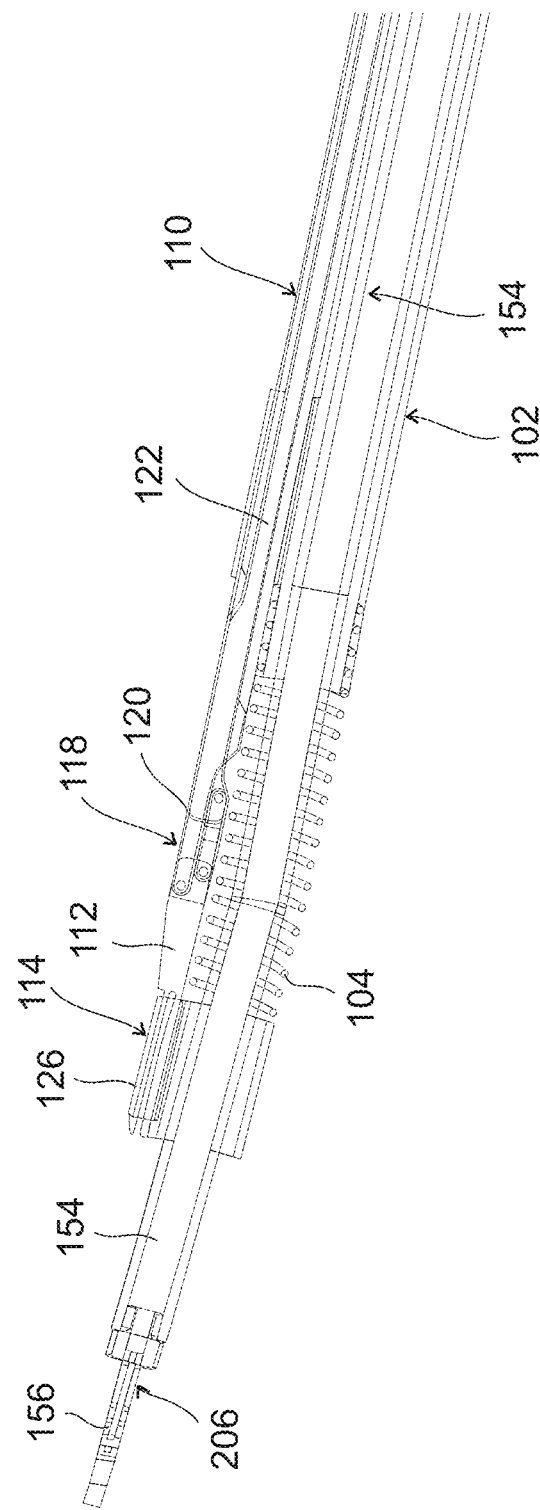
FIG. 6B is a simplified sectional view of a distal end of the working channel device of FIG. 4.

Reference is now made to FIG. 6A, which is a simplified sectional view of the handle containing an operating mechanism of the working channel device of FIG. 4 and to FIG. 6B, which is a simplified sectional view of a distal end of the working channel device of FIG. 4.

It is seen in FIG. 6A that endoscopic tool activation mechanism 200 is typically enclosed within tool handgrip 152 and is preferably fixedly attached to activating knob 160. It is also seen that a longitudinal opening 202 is formed on each side of the tool handgrip 152. An outwardly extending protrusion 204 of the endoscopic tool activation mechanism 200 extends through each of openings 202 and protrusions 204 are slidable within openings 202 once activating knob 160 is axially displaced.

Flexible shaft 154 is preferably fixedly retained within handgrip 152. A flexible wire mechanism 206 is attached at one side to the endoscopic tool 156 and at another side to the endoscopic tool activation mechanism 200.

It is appreciated that when the activating knob 160 is positioned at its distal position, protrusions 204 are located typically at the distal end of openings 202, in this position the flexible wire mechanism 206 is not activated and the endoscopic tool 156 is closed. Once the activating knob 160 is displaced axially proximally to its proximal position, it displaces the protrusions 204 proximally along openings 202 due to fixed attachment of the endoscopic tool activation mechanism 200 and the activating knob 160, thus activating the flexible wire mechanism 206 and consequently activating the endoscopic tool 156, such as for example opening the needle.

It is further particularly seen in FIGS. 6A, 6B, and 3B that locking button 162, which is disposed distally to activating knob 160 is adapted to lock the endoscopic tool 156 axially with respect to the working channel subassembly 100 at a desired axial location. Locking button 162 enables locking of the endoscopic tool 156 with respect to working channel subassembly 100 by means of a spring 208, which biases the locking button 162 distally, thus the inner surface of locking button 162 applies radial force on and inwardly deflects deformable leaves 210 formed on the outer surface of the distal end of tool handgrip 152 of the endoscopic tool sub-assembly 150. This engagement between the locking button 162 and deformable leaves 210 results in increased friction between handgrip 130 and endoscopic tool subassembly 150, thus axially locking the endoscopic tool 156 with respect to the working channel subassembly 100, in this case in an extended orientation of the endoscopic tool 156.

It is additionally seen in FIG. 6A that the hollow shaft 102 is fixedly attached to handgrip 130 of the working shaft subassembly 100. The spine cover 122 is also fixedly attached to handgrip 130 and spine pushrod 120 is fixedly attached to working channel articulating knob 140, having an inner helical groove path 222 (shown further in FIGS. 12B & 15B), so that upon rotation of working channel articulating knob 140, the spine pushrod 120 is axially distally displaced due to displacement along inner helical groove path 222. Axial displacement of spine pushrod 120 causes bending of articulating joint 118, and thus bending of hollow shaft 102, and in turn bending of flexible shaft 154 of the endoscopic tool subassembly 150.

It is further seen in FIG. 6A that a coil spring 224 is disposed within working channel articulating knob 140 and the spring 224 is supported at its distal end on the inner proximally facing surface of working channel articulating knob 140 and at its proximal end on a locking element 226. The locking element 226, as particularly shown in FIG. 3B, includes a disc element 228 and proximally spaced outwardly extending snap engagement ears 230 which are engaged with an inner threading 232 of locking knob 142.

It is appreciated that each bending angle of the articulating joint 118, and as a consequence of the hollow shaft 102 and flexible shaft 154, can be temporarily locked by means of rotation of locking knob 142, which locks further rotation of working channel articulating knob 140. The working channel articulating knob 140 is biased to the proximal orientation of spine pushrod 120, in which the articulating joint 118 is not bent, by means of the biasing force of spring 224.

It is particularly seen in FIG. 6B that the articulating joint 118 is in its non-bent orientation and thus flexible shaft 154 is not bent and endoscopic tool 156 extends substantially along longitudinal axis 155. Additionally, preferably the endoscopic tool 156 and a portion of the flexible shaft 154 extends from hollow shaft 102 of the working channel subassembly 100 in this second operative orientation.

It is a particular feature of an embodiment of the present invention that the working channel device has various degrees of freedom, such that the endoscopic tool subassembly 150 can be manually rotated with respect to the working channel subassembly 100 The entire working channel assembly 170 can be manually rotated within the patient body in order to introduce the endoscopic tool 156 at a different orientation.

It is appreciated that the articulating joint 118 can be initially positioned at a non-bent orientation and bending of the articulating joint at angles of 0-90° with respect to longitudinal axis 155 is enabled by working channel articulating knob 140. Alternatively, the articulating joint 118 can be initially positioned at angle with respect to longitudinal axis 155, such as −45° and then bending of the articulation joint 118 up to an angle of +45° with respect to longitudinal axis 155 is enabled by working channel articulating knob 140.

It is further appreciated that various endoscopic tools may be repeatedly interchanged within the working channel subassembly 100 during a single procedure. It is appreciated that various tools can be used, such as tools useful for arthroscopy, laparoscopy and other medical applications.

Figure 7:
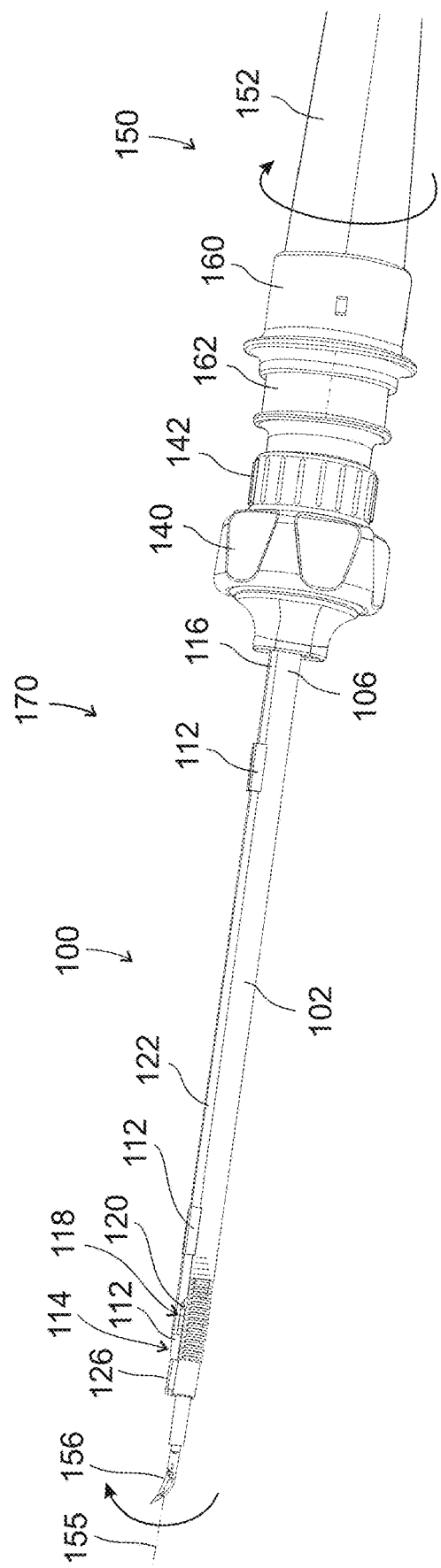
FIG. 7 is a simplified pictorial illustration of a working channel device having an endoscopic tool inserted therethrough, the working channel device is shown in a third operative orientation and is constructed and operative in accordance with an embodiment of the present invention.
Figure 8A:
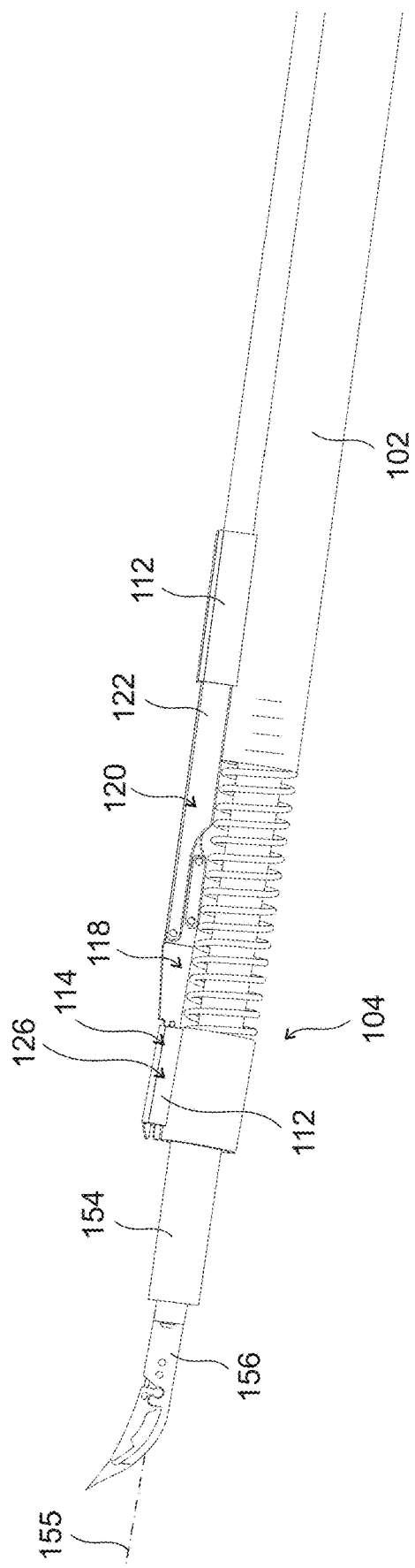
FIG. 8A is a simplified first side enlargement view of a distal end of the working channel device of FIG. 7.

Reference is now made to FIG. 7, which is a simplified pictorial illustration of the working channel device 170 having endoscopic tool subassembly 150 inserted therethrough, the working channel device is shown in a third operative orientation and is constructed and operative in accordance with an embodiment of the present invention. Reference is additionally made to FIG. 8A, which is a simplified first side enlargement view of a distal end of the working channel device 170 of FIG. 7 and to FIG. 8B, which is a simplified second side enlargement view of a distal end of the working channel device 170 of FIG. 7.

An assembled working channel device 170 having an endoscopic tool inserted therethrough is seen in FIG. 7.

It is a particular feature of an embodiment of the present invention that the endoscopic tool subassembly 150 is slidably inserted into the working channel subassembly 100 to form a single working channel device 170 with a single multi-functional handle enabling various axial and rotational movements of the endoscopic tool 156 within the body of a patient.

The endoscopic tool subassembly 150 is slidably received into working channel subassembly 100 and both are arranged along a single longitudinal axis, axis 103 and axis 155, which are aligned.

Figure 8B:
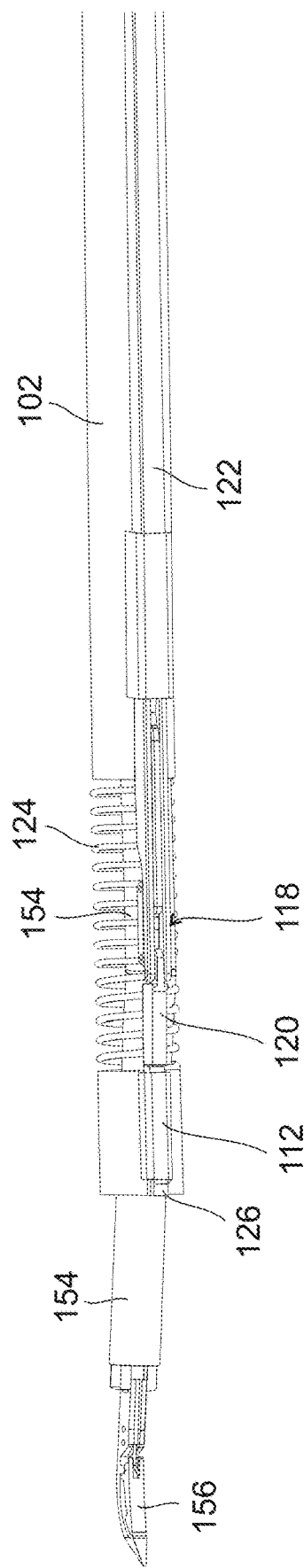
FIG. 8B is a simplified second side enlargement view of a distal end of the working channel device of FIG. 7.

The working channel device 170 is shown in a third operative orientation in FIGS. 7, 8A & 8B. In this third operative orientation, the following spatial relations exist:

The endoscopic tool 156 is shown in an un-activated closed orientation, as particularly seen in FIG. 8A.

The endoscopic tool 156 is positioned in its extended orientation with respect to hollow shaft 102, such that flexible shaft 154 and endoscopic tool 156 partially extends distally from hollow shaft 102. This extended orientation of the endoscopic tool 156 results from the fact that the locking knob 162 abuts locking knob 142 due to distal displacement of endoscopic tool subassembly into working channel subassembly 100. The endoscopic tool 156 may extend out of the hollow shaft 102 as far as 12 mm, for example.

It is further seen that in an embodiment of the present invention, in this third operative orientation, the endoscopic tool 156 extends along a plane which is aligned with the plane along which spine 110 extends. It is appreciated that alternatively, the endoscopic tool 156 can be initially oriented at any other angle of rotation about its longitudinal axis.

It is a particular feature of an embodiment of the present invention that the endoscopic tool subassembly 150 has various degrees of freedom within the working channel sub-assembly 100, such as rotation of the endoscopic tool subassembly 150 about its axis, axial relative movement of the endoscopic tool subassembly 150 relative to the working channel subassembly 100 and activation of the endoscopic tool 156 while the endoscopic tool subassembly 150 is mounted within the working channel subassembly 100.

The working channel subassembly 100 is positioned in a non-bent orientation in FIGS. 7, 8A & 8B due to the fact that the working channel articulating knob 140 is in a first non-activated orientation.

It is a particular feature of an embodiment of the present invention that the flexible shaft 154 of the endoscopic tool subassembly 150 follows the geometry of the hollow shaft 102, whereas spine 110 provides the required rigidity to the hollow shaft 102 and as a consequence to flexible shaft 154. Once the spine 110 is bent, the hollow shaft 102 is bent with it, since the hollow shaft 102 is locked to the spine 110 and in turn the flexible shaft 154 is bent as well and enables articulation of the endoscopic tool 156 with respect to longitudinal axis 155.

Figure 9A:
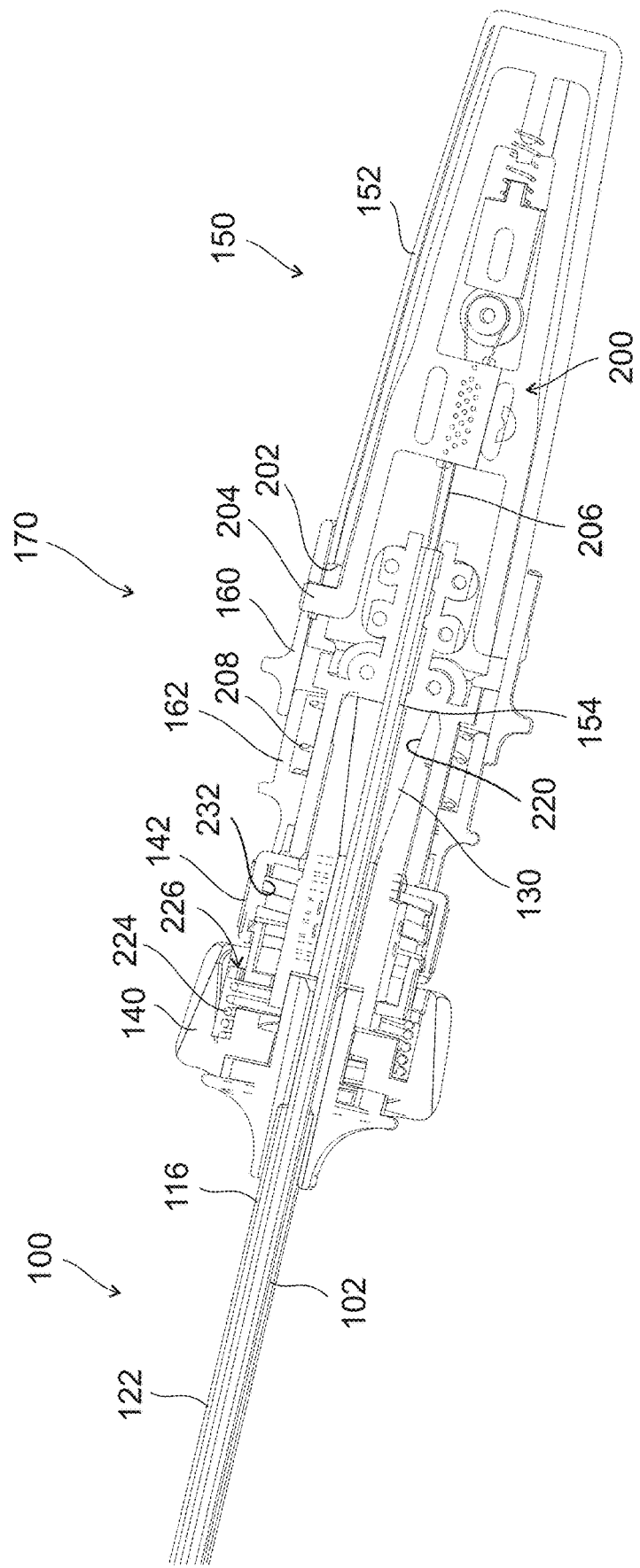
FIG. 9A is a simplified sectional view of the handle containing an operating mechanism of the working channel device of FIG. 7.

Reference is now made to FIG. 9A, which is a simplified sectional view of the handle containing an operating mechanism of the working channel device 170 of FIG. 7 and to FIG. 9B, which is a simplified sectional view of a distal end of the working channel device 170 of FIG. 7.

It is seen in FIG. 9A that endoscopic tool activation mechanism 200 is typically enclosed within tool handgrip 152 and is preferably fixedly attached to activating knob 160. It is also seen that a longitudinal opening 202 is formed on each side of the tool handgrip 152. An outwardly extending protrusion 204 of the endoscopic tool activation mechanism 200 extends through each of openings 202 and protrusions 204 are slidable within openings 202 once activating knob 160 is axially displaced.

Flexible shaft 154 is preferably fixedly retained within handgrip 152. A flexible wire mechanism 206 is attached at one side to the endoscopic tool 156 and at another side to the endoscopic tool activation mechanism 200.

It is appreciated that when the activating knob 160 is positioned at its distal position, protrusions 204 are located typically at the distal end of openings 202, in this position the flexible wire mechanism 206 is not activated and the endoscopic tool 156 is closed. Once the activating knob 160 is displaced axially proximally to its proximal position, it displaces the protrusions 204 proximally along openings 202 due to fixed attachment of the endoscopic tool activation mechanism 200 and the activating knob 160, thus activating the flexible wire mechanism 206 and consequently activating the endoscopic tool 156, such as for example opening the needle.

It is further particularly seen in FIGS. 9A, 9B, and 3B that locking button 162, which is disposed distally to activating knob 160 is adapted to lock the endoscopic tool 156 axially with respect to the working channel subassembly 100 at a desired axial location. Locking button 162 enables locking of the endoscopic tool 156 with respect to working channel subassembly 100 by means of a spring 208, which biases the locking button 162 distally, thus the inner surface of locking button 162 applies radial force on and inwardly deflects deformable leaves 210 formed on the outer surface of the distal end of tool handgrip 152 of the endoscopic tool sub-assembly 150. This engagement between the locking button 162 and deformable leaves 210 results in increased friction between handgrip 130 and endoscopic tool sub-assembly 150, thus axially locking the endoscopic tool 156 with respect to the working channel subassembly 100.

It is additionally seen in FIG. 9A that the hollow shaft 102 is fixedly attached to handgrip 130 of the working shaft subassembly 100. The spine cover 122 is also fixedly attached to handgrip 130 and spine pushrod 120 is fixedly attached to working channel articulating knob 140, having an inner helical groove path 222 (shown further in FIGS. 12B & 15B), so that upon rotation of working channel articulating knob 140, the spine pushrod 120 is axially distally displaced due to displacement along inner helical groove path 222. Axial displacement of spine pushrod 120 causes bending articulating joint 118, and thus bending of hollow shaft 102, and in turn bending of flexible shaft 154 of the endoscopic tool subassembly 150.

It is further seen in FIG. 9A that a coil spring 224 is disposed within working channel articulating knob 140 and the spring 224 is supported at its distal end on the inner proximally facing surface of working channel articulating knob 140 and at its proximal end on a locking element 226. The locking element 226, as particularly shown in FIGS. 12C-D, includes a disc element 228 and proximally spaced outwardly extending snap engagement ears 230 which are engaged with an inner threading 232 of locking knob 142.

It is appreciated that each bending angle of the articulating joint 118, and as a consequence of the hollow shaft 102 and flexible shaft 154 can be temporarily locked by means of rotation of locking knob 142, which locks further rotation of working channel articulating knob 140. The working channel articulating knob 140 is biased to the proximal orientation of spine pushrod 120, in which the articulating joint 118 is non-bent, by means of the biasing force of spring 224.

It is particularly seen in FIG. 9B that the articulating joint 118 is in its non-bent orientation and thus flexible shaft 154 is not bent and endoscopic tool 156 extends substantially along longitudinal axis 155. Additionally, preferably a portion of flexible shaft 154 and the endoscopic tool 156 extend distally from hollow shaft 102 of the working channel subassembly 100.

It is a particular feature of an embodiment of the present invention that the working channel device has various degrees of freedom, such that the endoscopic tool subassembly 150 can be manually rotated with respect to the working channel subassembly 100. The entire working channel assembly 170 can be manually rotated within the patient body in order to introduce the endoscopic tool 156 at a different orientation.

It is particularly seen in FIGS. 7-9A that the endoscopic tool subassembly 150 is rotated with respect to working channel subassembly 100, thus endoscopic tool 156 generally lies along a plane which is aligned along which the spine 110 extends.

It is appreciated that the articulating joint 118 can be initially positioned at a non-bent orientation and bending of the articulating joint at angles of 0-90° with respect to longitudinal axis 155 is enabled by working channel articulating knob 140. Alternatively, the articulating joint 118 can be initially positioned at angle with respect to longitudinal axis 155, such as −45° and then bending of the articulation joint 118 up to an angle of +45° with respect to longitudinal axis 155 is enabled by working channel articulating knob 140.

It is further appreciated that various endoscopic tools may be repeatedly interchanged within the working channel subassembly 100 during a single procedure. It is appreciated that various tools can be used, such as tools useful for arthroscopy, laparoscopy and other medical applications.

Figure 10:
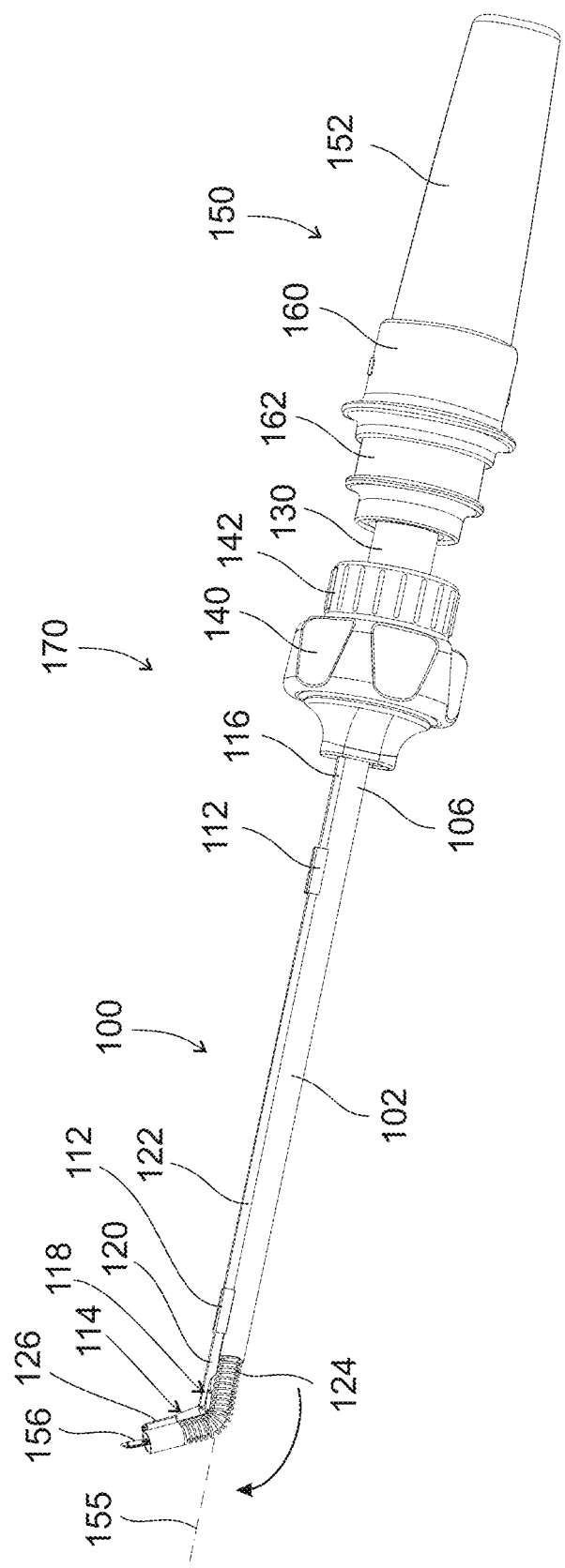
FIG. 10 is a simplified pictorial illustration of a working channel device having an endoscopic tool inserted therethrough, the working channel device is shown in a fourth operative orientation and is constructed and operative in accordance with an embodiment of the present invention.
Figure 11A:
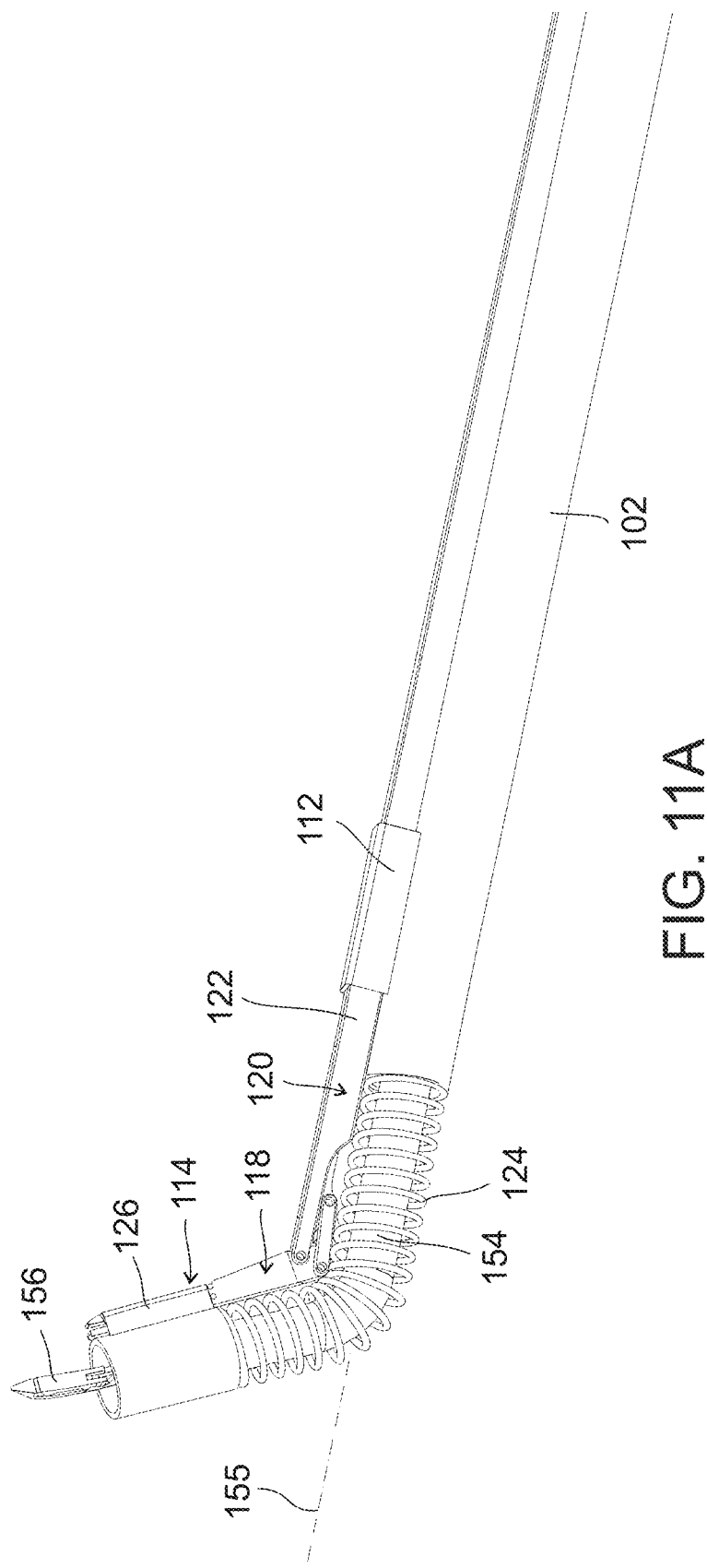
FIG. 11A is a simplified first side enlargement view of a distal end of the working channel device of FIG. 10.

Reference is now made to FIG. 10, which is a simplified pictorial illustration of the working channel device 170 having an endoscopic tool inserted therethrough, the working channel device 170 is shown in a fourth operative orientation and is constructed and operative in accordance with an embodiment of the present invention. Reference is additionally made to FIG. 11A, which is a simplified first side enlargement view of a distal end of the working channel device 170 of FIG. 10 and to FIG. 11B, which is a simplified second side enlargement view of a distal end of the working channel device of FIG. 10.

An assembled working channel device 170 having an endoscopic tool inserted therethrough is seen in FIG. 10.

It is a particular feature of an embodiment of the present invention that the endoscopic tool subassembly 150 is slidably inserted into the working channel subassembly 100 to form a single working channel device 170 with a single multi-functional handle enabling various axial and rotational movements of the endoscopic tool 156 within the body of a patient.

The endoscopic tool subassembly 150 is slidably received into working channel subassembly 100 and both are arranged along a single longitudinal axis, axis 103 and axis 155, which are aligned.

Figure 11B:
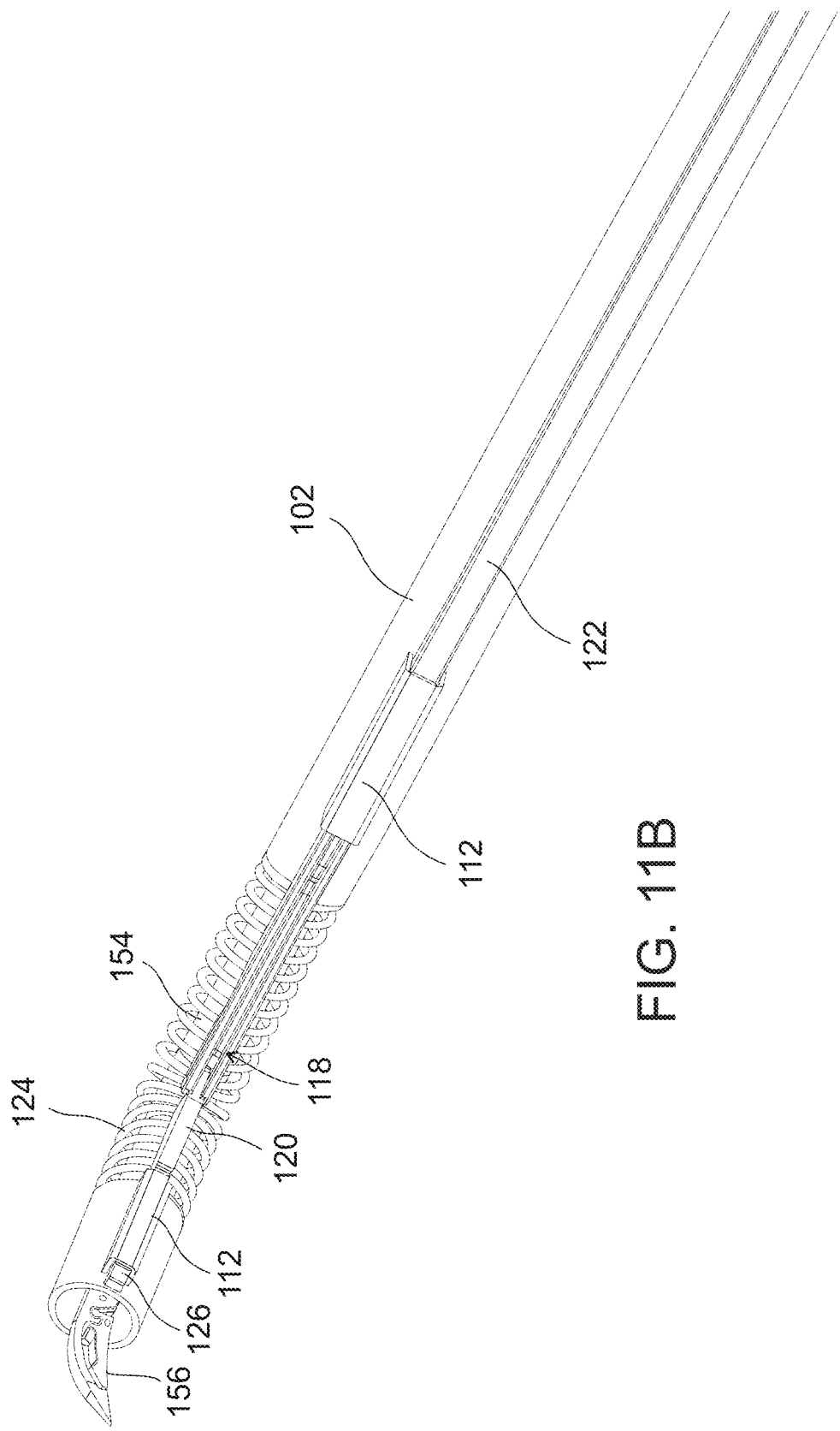
FIG. 11B is a simplified second side enlargement view of a distal end of the working channel device of FIG. 10.

The working channel device 170 is shown in a fourth operative orientation in FIGS. 10, 11A & 11B. In this fourth operative orientation, the following spatial relations exist:

The endoscopic tool 156 is shown in an un-activated closed orientation, as particularly seen in FIG. 8A.

The endoscopic tool 156 is positioned in its retracted orientation with respect to hollow shaft 102, such that flexible shaft 154 is fully enclosed within hollow shaft 102 and endoscopic tool 156 partially extends distally from hollow shaft 102. This retracted orientation of the endoscopic tool 156 results from the fact that the locking knob 162 is proximally spaced from locking knob 142 due to proximal displacement of endoscopic tool subassembly out of working channel subassembly 100 as compared with the working channel device 170 shown in FIG. 7.

It is further seen that in an embodiment of the present invention, in this fourth operative orientation, the endoscopic tool 156 extends along a plane which is disposed transversely to the plane along which spine 110 extends. It is appreciated that alternatively, the endoscopic tool 156 can be initially oriented at any other angle of rotation about its longitudinal axis.

It is a particular feature of an embodiment of the present invention that the endoscopic tool subassembly 150 has various degrees of freedom within the working channel sub-assembly 100, such as rotation of the endoscopic tool subassembly 150 about its axis, axial relative movement of the endoscopic tool subassembly 150 relative to the working channel subassembly 100 and activation of the endoscopic tool 156 while the endoscopic tool subassembly 150 is mounted within the working channel subassembly 100.

The working channel subassembly 100 is positioned in a bent orientation in FIGS. 10, 11A & 11B due to the fact that the working channel articulating knob 140 is in a second activated orientation.

It is a particular feature of an embodiment of the present invention that the flexible shaft 154 of the endoscopic tool subassembly 150 follows the geometry of the hollow shaft 102, whereas spine 110 provides the required rigidity to the hollow shaft 102 and as a consequence to flexible shaft 154. Once the spine 110 is bent, the hollow shaft 102 is bent with it, since the hollow shaft 102 is locked to the spine 110 and in turn the flexible shaft 154 is bent as well and enables articulation of the endoscopic tool 156 with respect to longitudinal axis 155.

Figure 12A:
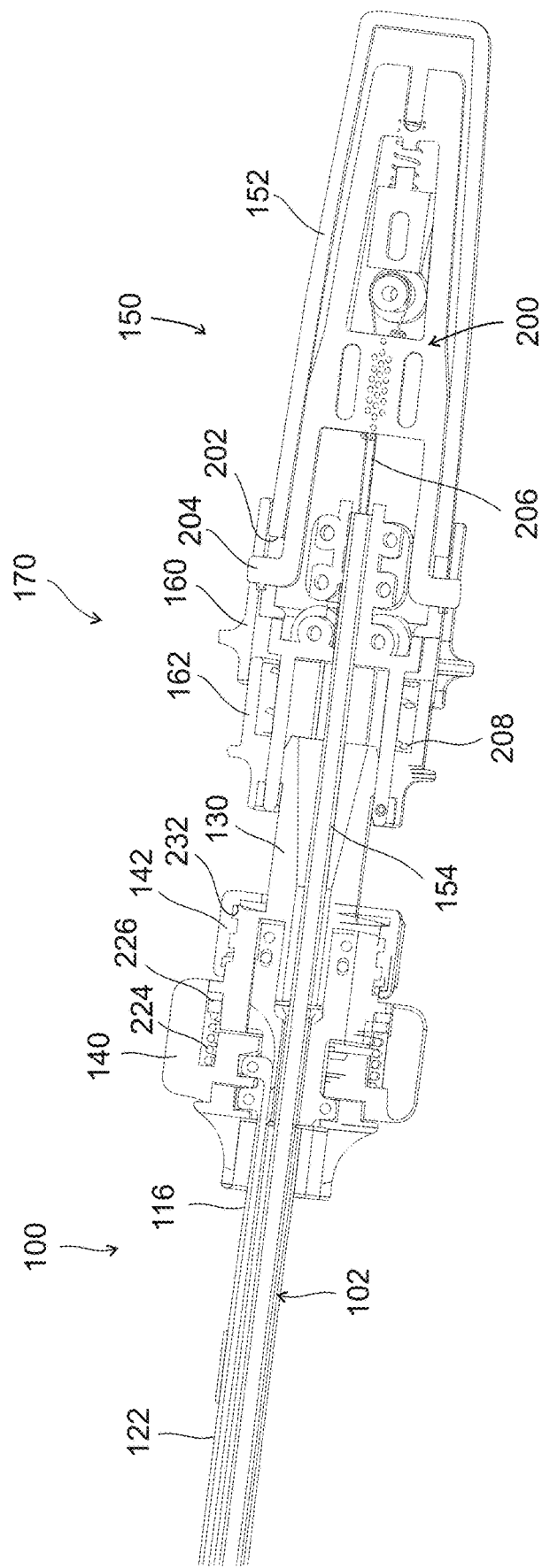
FIG. 12A is a simplified sectional view of the handle containing an operating mechanism of the working channel device of FIG. 10.
Figure 12B:
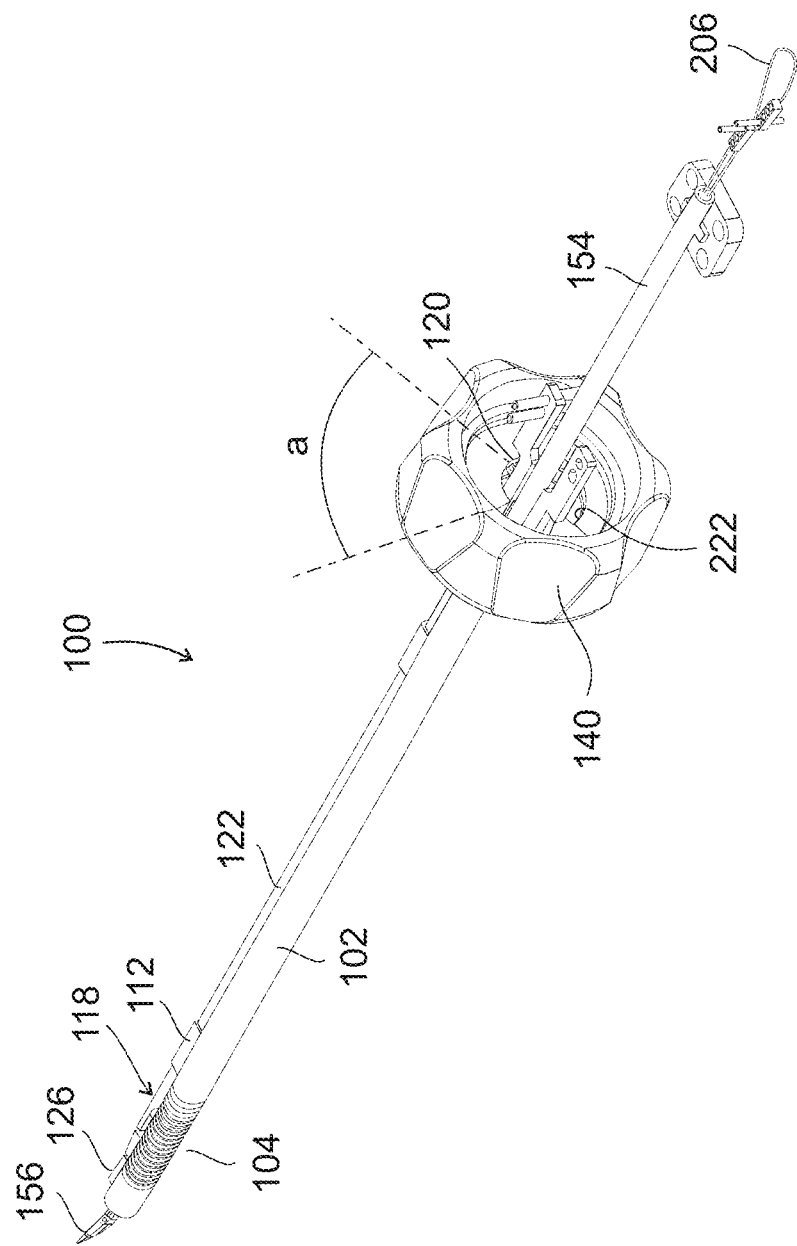
FIG. 12B is a simplified partial pictorial illustration of the handle containing part of an operating mechanism of the working channel device of FIG. 10.
Figure 12C:
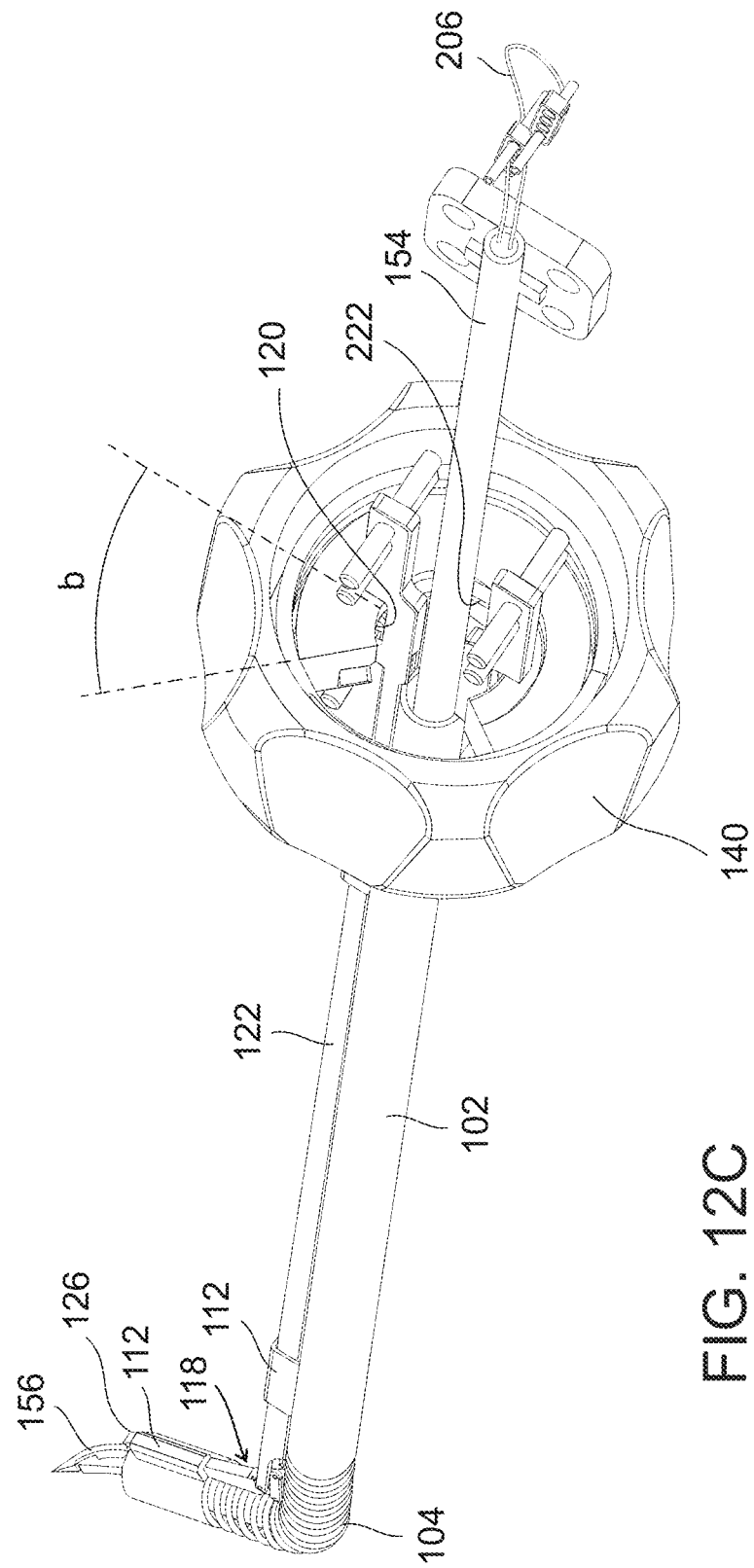
FIG. 12C is a simplified different partial pictorial illustration of the handle containing part of an operating mechanism of the working channel device of FIG. 10.
Figure 12D:
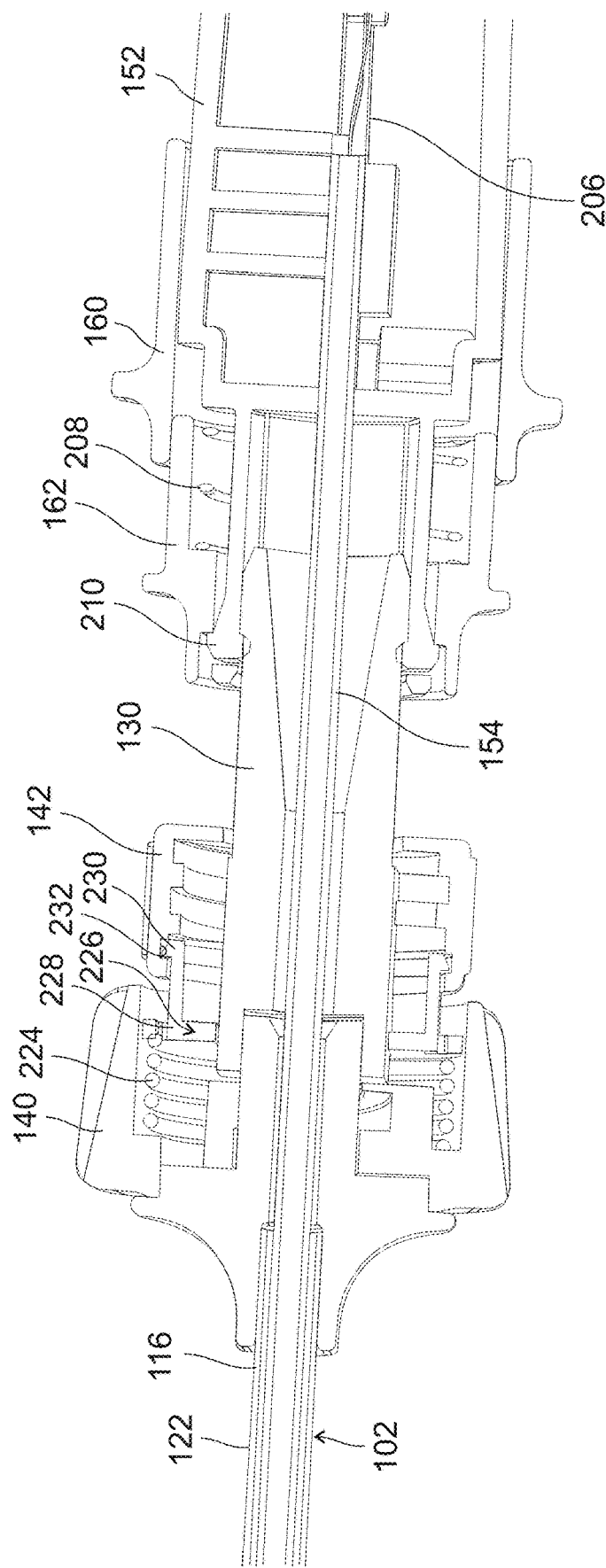
FIG. 12D is a simplified partial sectional view of the handle containing part of an operating mechanism of the working channel device of FIG. 10.
Figure 12E:
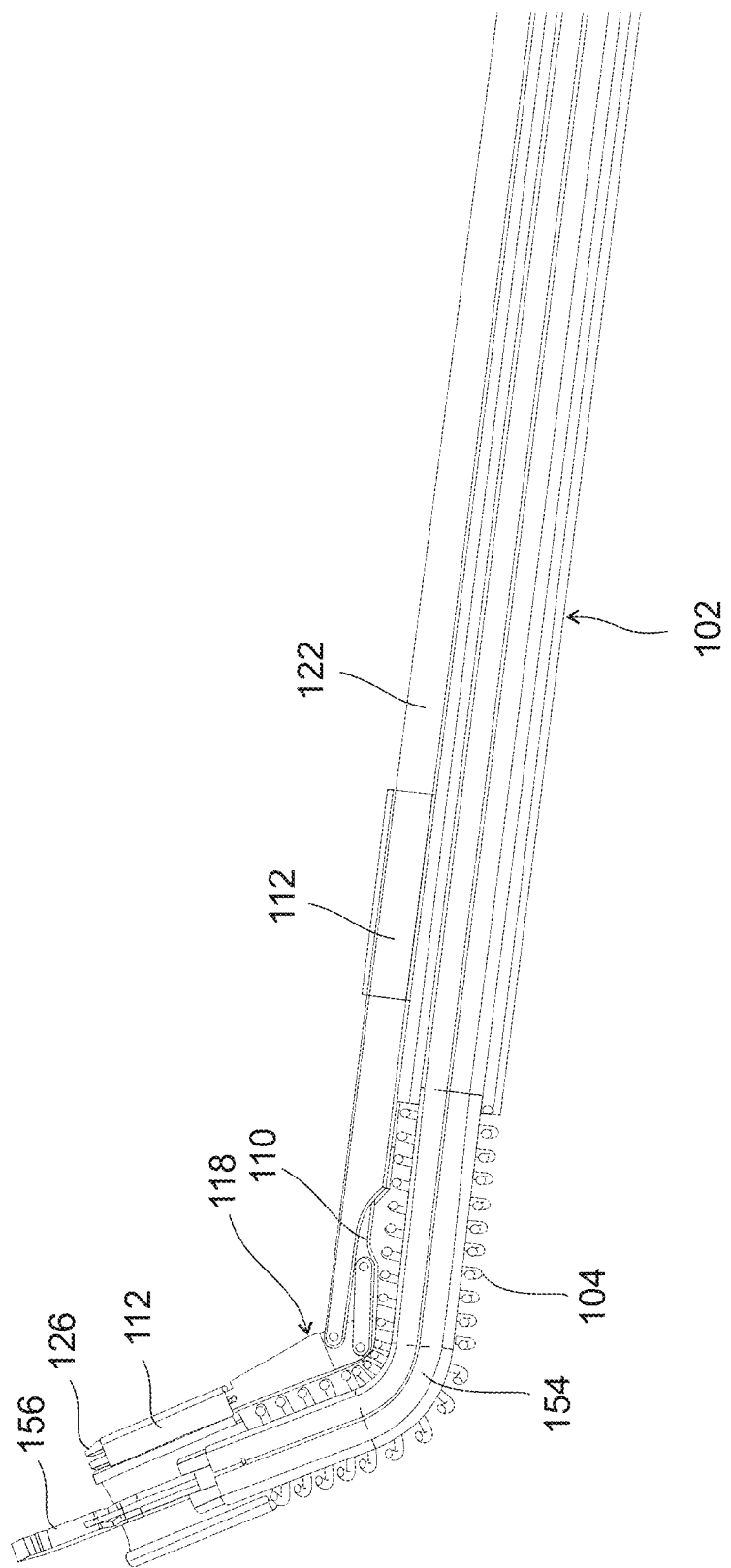
FIG. 12E is a simplified sectional view of a distal end of the working channel device of FIG. 10.

Reference is now made to FIG. 12A, which is a simplified sectional view of the handle containing an operating mechanism of the working channel device of FIG. 10 and to FIG. 12B, which is a simplified partial pictorial illustration of the handle containing part of an operating mechanism of the working channel device of FIG. 10 and to FIG. 12C, which is a simplified different partial pictorial illustration of the handle containing part of an operating mechanism of the working channel device of FIG. 10 and to FIG. 12D, which is a simplified partial sectional view of the handle containing part of an operating mechanism of the working channel device of FIG. 10 and to FIG. 12E, which is a simplified sectional view of a distal end of the working channel device of FIG. 10.

It is seen in FIG. 12A that endoscopic tool activation mechanism 200 is typically enclosed within tool handgrip 152 and is preferably fixedly attached to activating knob 160. It is also seen that a longitudinal opening 202 is formed on each side of the tool handgrip 152. An outwardly extending protrusion 204 of the endoscopic tool activation mechanism 200 extends through each of openings 202 and protrusions 204 are slidable within openings 202 once activating knob 160 is axially displaced.

Flexible shaft 154 is preferably fixedly retained within handgrip 152. A flexible wire mechanism 206 is attached at one side to the endoscopic tool 156 and at another side to the endoscopic tool activation mechanism 200.

It is appreciated that when the activating knob 160 is positioned at its distal position, protrusions 204 are located typically at the distal end of openings 202, in this position the flexible wire mechanism 206 is not activated and the endoscopic tool 156 is closed. Once the activating knob 160 is displaced axially proximally to its proximal position, it displaces the protrusions 204 proximally along openings 202 due to fixed attachment of the endoscopic tool activation mechanism 200 and the activating knob 160, thus activating the flexible wire mechanism 206 and consequently activating the endoscopic tool 156, such as for example opening the needle.

It is further particularly seen in FIGS. 12A & 12D that locking button 162, which is disposed distally to activating knob 160 is adapted to lock the endoscopic tool 156 axially with respect to the working channel subassembly 100 at a desired axial location. Locking button 162 enables locking of the endoscopic tool 156 with respect to working channel subassembly 100 by means of a spring 208, which biases the locking button 162 distally, thus the inner surface of locking button 162 applies radial force on and inwardly deflects deformable leaves 210 formed on the outer surface of the distal end of tool handgrip 152 of the endoscopic tool sub-assembly 150. This engagement between the locking button 162 and deformable leaves 210 results in increased friction between handgrip 130 and endoscopic tool subassembly 150, thus axially locking the endoscopic tool 156 with respect to the working channel subassembly 100.

It is additionally seen in FIGS. 12A-12C that the hollow shaft 102 is fixedly attached to handgrip 130 of the working shaft subassembly 100. The spine cover 122 is also fixedly attached to handgrip 130 and spine pushrod 120 is fixedly attached to working channel articulating knob 140, having an inner helical groove path 222 (shown particularly in FIGS. 12B & 12C), so that upon rotation of working channel articulating knob 140, the spine pushrod 120 is axially distally displaced due to displacement along inner helical groove path 222. Axial displacement of spine pushrod 120 causes bending of articulating joint 118, and thus bending of hollow shaft 102, and in turn bending of flexible shaft 154 of the endoscopic tool subassembly 150.

It is particularly seen from comparison of FIG. 12B and FIG. 12C that the proximal end of spine pushrod 120 is supported within helical groove 222 of the articulating knob 140. It is seen in FIG. 12B, in which the hollow shaft is shown in a non-bent operative orientation that the proximal end of the spine pushrod 120 is located at an angle "a" with respect to the edge of the spiral groove 222. It is seen in FIG. 12C, in which the hollow shaft is shown in a bent operative orientation that the proximal end of the spine pushrod 120 is located at an angle "b" with respect to the edge of the spiral groove 222. It is appreciated that angle "b" is preferably smaller than angle "a," thus it is understood that rotation of articulating knob 140, urges displacement of proximal end of the spine pushrod 120 along the helical grove 222, thus causing axial displacement of the spine pushrod 120 and as a consequence articulating of joint 118 and bending of the hollow shaft 102, which in turn causes bending of the flexible shaft 154 carrying the endoscopic tool 156.

It is further seen in FIG. 12D that coil spring 224 is disposed within working channel articulating knob 140 and the spring 224 is supported at its distal end on the inner proximally facing surface of working channel articulating knob 140 and at its proximal end on a locking element 226. The locking element 226, as particularly shown in FIG. 12D, includes a disc element 228 and proximally spaced outwardly extending snap engagement ears 230 which are engaged with an inner threading 232 of locking knob 142.

It is appreciated that each bending angle of the articulating joint 118, and as a consequence of the hollow shaft 102 and flexible shaft 154 can be temporarily locked by means of rotation of locking knob 142, which locks further rotation of working channel articulating knob 140. The working channel articulating knob 140 is biased to the proximal orientation of spine pushrod 120, in which the articulating joint 118 is not bent, by means of the biasing force of spring 224.

It is particularly seen in FIG. 12E that the articulating joint 118 is in its bent orientation and thus flexible shaft 154 is bent and endoscopic tool 156 extends substantially at an angle with respect to longitudinal axis 155. Additionally, in this operative orientation only the endoscopic tool 156 extend distally from hollow shaft 102 of the working channel subassembly 100.

It is a particular feature of an embodiment of the present invention that the working channel device has various degrees of freedom, such that the working channel device has various degrees of freedom, such that the endoscopic tool subassembly 150 can be manually rotated with respect to the working channel subassembly 100. The entire working channel assembly 170 can be manually rotated within the patient body in order to introduce the endoscopic tool 156 at a different orientation.

It is particularly seen in FIGS. 10-11B that the endoscopic tool subassembly 150 is in a non-rotated operative orientation with respect to working channel subassembly 100, thus endoscopic tool 156 generally lies along a plane which extends transversely with respect to the plane along which the spine 110 extends.

It is appreciated that the articulating joint 118 can be initially positioned at a non-bent orientation and bending of the articulating joint at angles of 0-90° with respect to longitudinal axis 155 is enabled by working channel articulating knob 140. Alternatively, the articulating joint 118 can be initially positioned at angle with respect to longitudinal axis 155, such as −45° and then bending of the articulation joint 118 up to an angle of +45° with respect to longitudinal axis 155 is enabled by working channel articulating knob 140.

It is further appreciated that various endoscopic tools may be repeatedly interchanged within the working channel subassembly 100 during a single procedure. It is appreciated that various tools can be used, such as tools useful for arthroscopy, laparoscopy and other medical applications.

Figure 13:
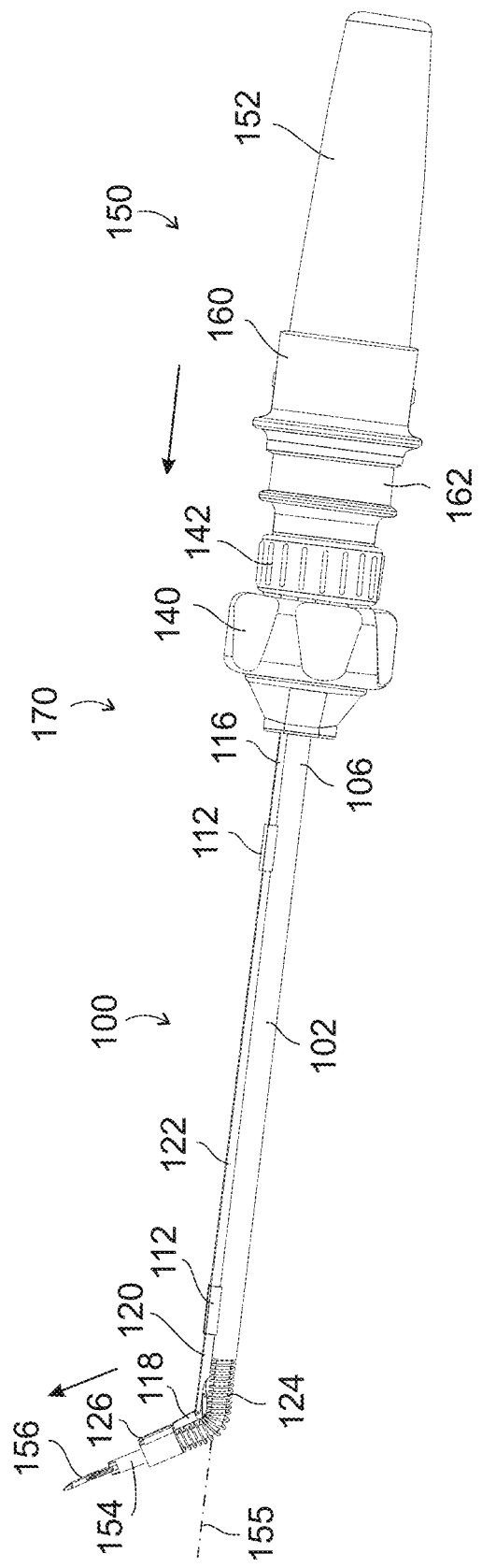
FIG. 13 is a simplified pictorial illustration of a working channel device having an endoscopic tool inserted therethrough, the working channel device is shown in a fifth operative orientation and is constructed and operative in accordance with an embodiment of the present invention.
Figure 14A:
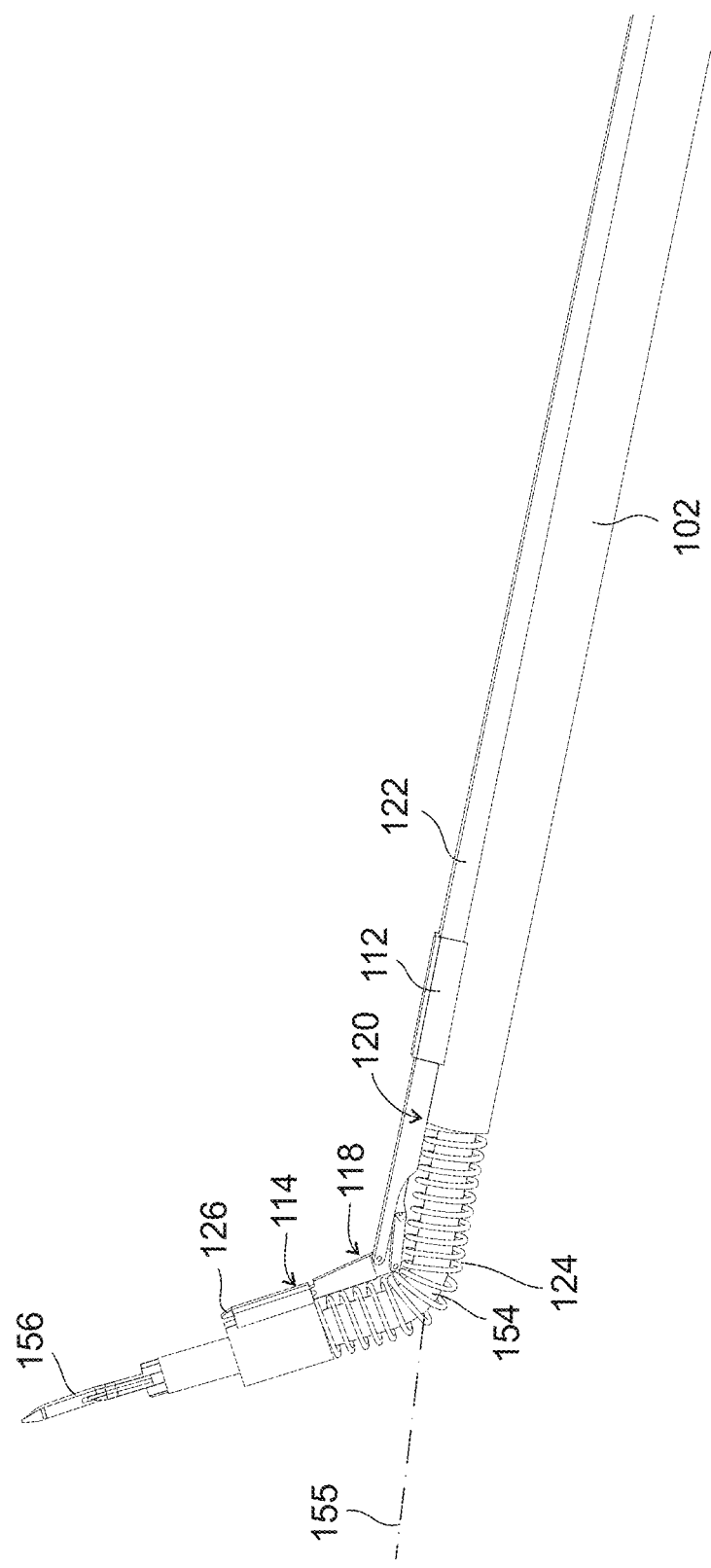
FIG. 14A is a simplified first side enlargement view of a distal end of the working channel device of FIG. 13.

Reference is now made to FIG. 13, which is a simplified pictorial illustration of a working channel device having an endoscopic tool 170 inserted therethrough, the working channel device is shown in a fifth operative orientation and is constructed and operative in accordance with an embodiment of the present invention. Reference is additionally made to FIG. 14A, which is a simplified first side enlargement view of a distal end of the working channel device of FIG. 13 and to FIG. 14B, which is a simplified second side enlargement view of a distal end of the working channel device of FIG. 13. Reference is additionally made to FIG. 15A, which is a simplified sectional view of the handle containing an operating mechanism of the working channel device of FIG. 13 and to FIG. 15B, which is a simplified sectional view of a distal end of the working channel device of FIG. 13.

An assembled working channel device 170 having an endoscopic tool inserted therethrough is seen in FIG. 13.

It is a particular feature of an embodiment of the present invention that the endoscopic tool subassembly 150 is slidably inserted into the working channel subassembly 100 to form a single working channel device 170 with a single multi-functional handle enabling various axial and rotational movements of the endoscopic tool 156 within the body of a patient.

The endoscopic tool subassembly 150 is slidably received into working channel subassembly 100 and both are arranged along a single longitudinal axis, axis 103 and axis 155, which are aligned.

Figure 14B:
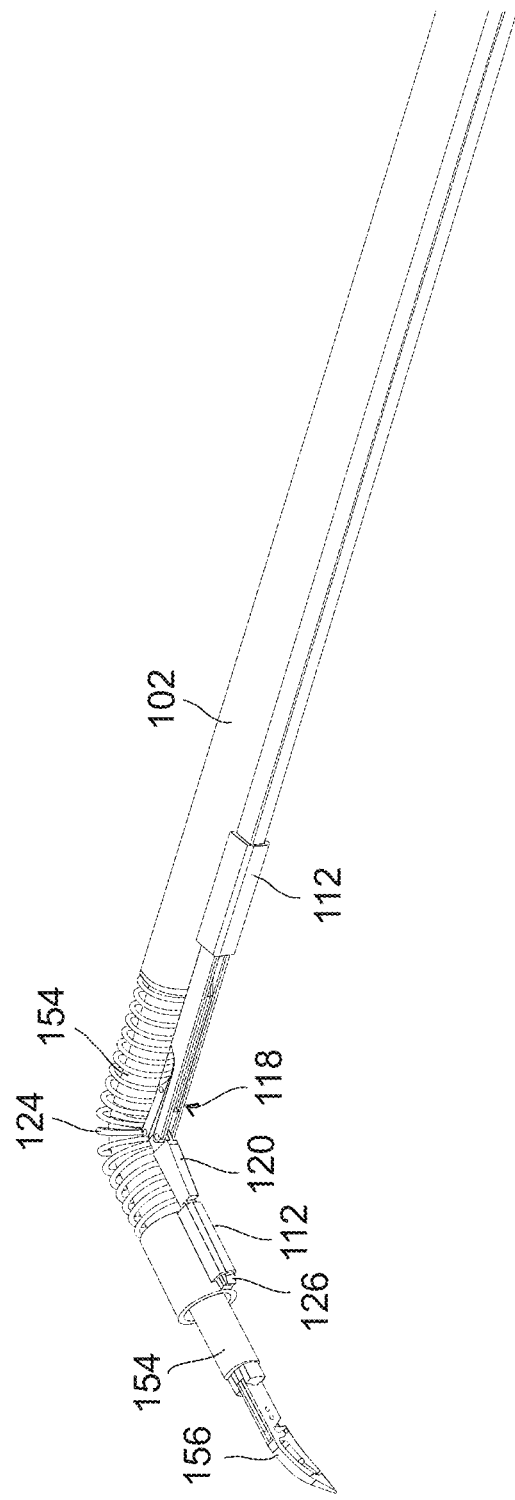
FIG. 14B is a simplified second side enlargement view of a distal end of the working channel device of FIG. 13.
Figure 15A:
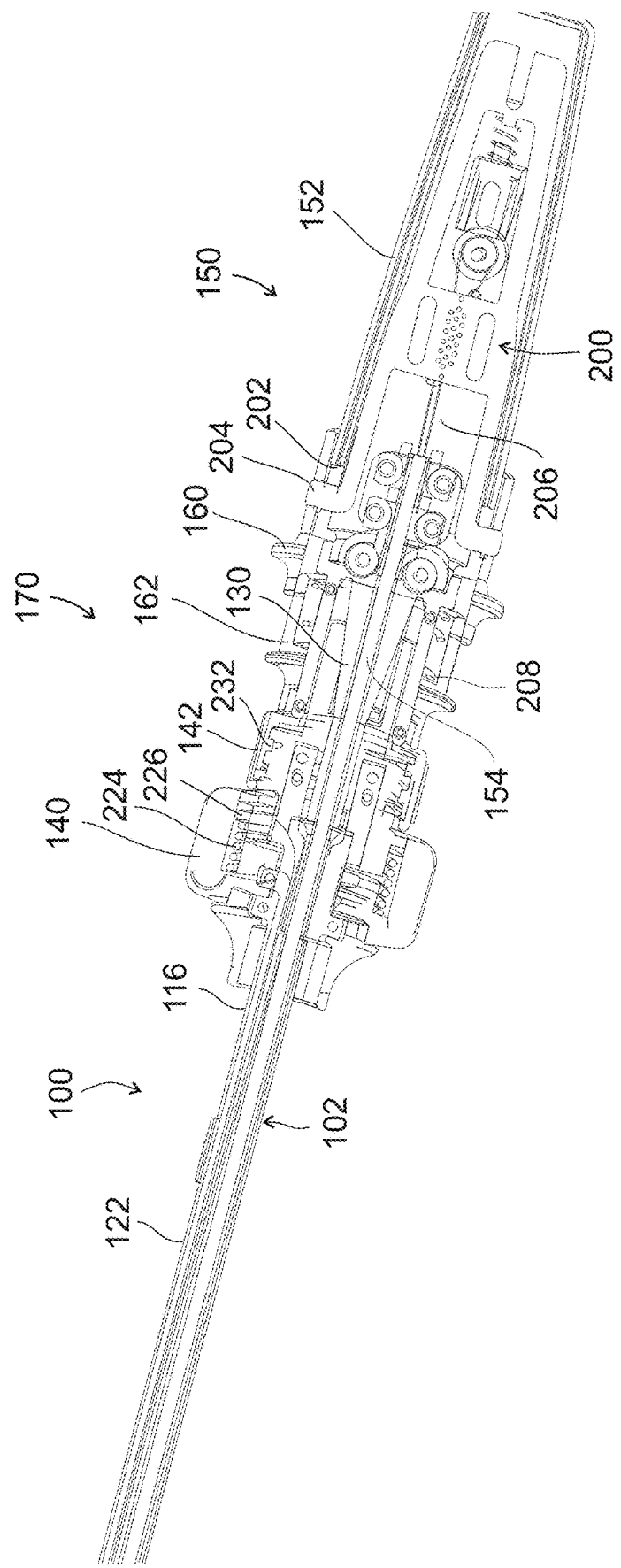
FIG. 15A is a simplified sectional view of the handle containing an operating mechanism of the working channel device of FIG. 13.

The working channel device 170 is shown in a fifth operative orientation in FIGS. 13, 14A & 14B. In this fifth operative orientation, the following spatial relations exist:

The endoscopic tool 156 is shown in an un-activated closed orientation, as particularly seen in FIG. 14A.

The endoscopic tool 156 is positioned in its extended orientation with respect to hollow shaft 102, such that flexible shaft 154 preferably partially extends distally from hollow shaft 102 and endoscopic tool 156 extends distally from hollow shaft 102. This extended orientation of the endoscopic tool 156 results from the fact that the locking knob 162 abuts locking knob 142 due to distal displacement of endoscopic tool subassembly into working channel subassembly 100.

It is further seen that in an embodiment of the present invention, in this fifth operative orientation, the endoscopic tool 156 extends along a plane which is disposed transversely to the plane along which spine 110 extends. It is appreciated that alternatively, the endoscopic tool 156 can be initially oriented at any other angle of rotation about its longitudinal axis.

It is a particular feature of an embodiment of the present invention that the endoscopic tool subassembly 150 has various degrees of freedom within the working channel sub-assembly 100, such as rotation of the endoscopic tool subassembly 150 about its axis, axial relative movement of the endoscopic tool subassembly 150 relative to the working channel subassembly 100 and activation of the endoscopic tool 156 while the endoscopic tool subassembly 150 is mounted within the working channel subassembly 100.

The working channel subassembly 100 is positioned in a bent orientation in FIGS. 13, 14A & 14B due to the fact that the working channel articulating knob 140 is in a second activated orientation.

It is a particular feature of an embodiment of the present invention that the flexible shaft 154 of the endoscopic tool subassembly 150 follows the geometry of the hollow shaft 102, whereas spine 110 provides the required rigidity to the hollow shaft 102 and as a consequence to flexible shaft 154. Once the spine 110 is bent, the hollow shaft 102 is bent with it, since the hollow shaft 102 is locked to the spine 110 and in turn the flexible shaft 154 is bent as well and enables articulation of the endoscopic tool 156 with respect to longitudinal axis 155.

Figure 15B:
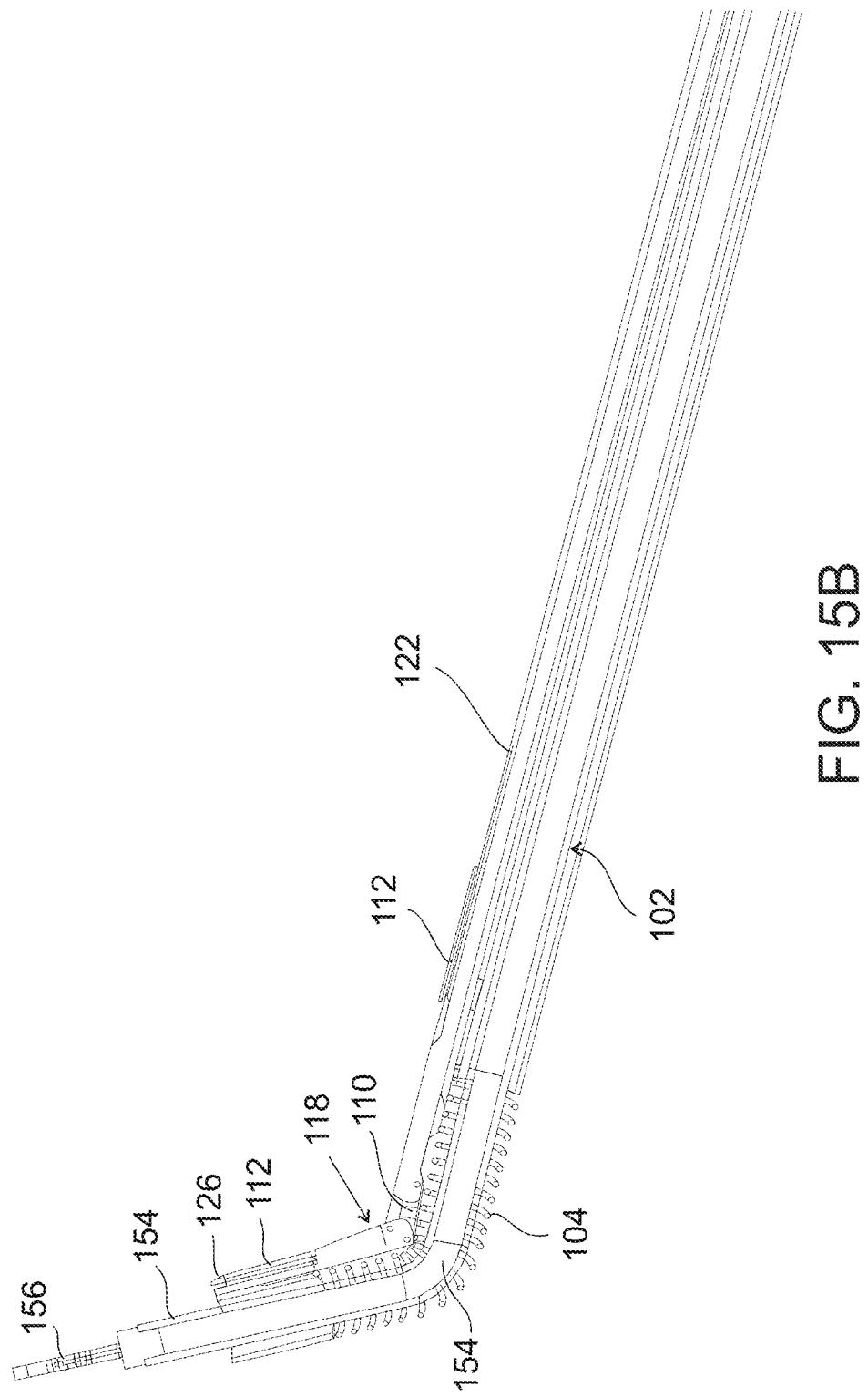
FIG. 15B is a simplified sectional view of a distal end of the working channel device of FIG. 13.

Reference is now made to FIG. 15A, which is a simplified sectional view of the handle containing an operating mechanism of the working channel device of FIG. 13 and to FIG. 15B, which is a simplified sectional view of a distal end of the working channel device of FIG. 13.

It is seen in FIG. 15A that endoscopic tool activation mechanism 200 is typically enclosed within tool handgrip 152 and is preferably fixedly attached to activating knob 160. It is also seen that a longitudinal opening 202 is formed on each side of the tool handgrip 152. An outwardly extending protrusion 204 of the endoscopic tool activation mechanism 200 extends through each of openings 202 and protrusions 204 are slidable within openings 202 once activating knob 160 is axially displaced.

Flexible shaft 154 is preferably fixedly retained within handgrip 152. A flexible wire mechanism 206 is attached at one side to the endoscopic tool 156 and at another side to the endoscopic tool activation mechanism 200.

It is appreciated that when the activating knob 160 is positioned at its distal position, protrusions 204 are located typically at the distal end of openings 202, in this position the flexible wire mechanism 206 is not activated and the endoscopic tool 156 is closed. Once the activating knob 160 is displaced axially proximally to its proximal position, it displaces the protrusions 204 proximally along openings 202 due to fixed attachment of the endoscopic tool activation mechanism 200 and the activating knob 160, thus activating the flexible wire mechanism 206 and consequently activating the endoscopic tool 156, such as for example opening the needle.

It is further seen in FIGS. 15A and 12D that locking button 162, which is disposed distally to activating knob 160 is adapted to lock the endoscopic tool 156 axially with respect to the working channel subassembly 100 at a desired axial location. Locking button 162 enables locking of the endoscopic tool 156 with respect to working channel subassembly 100 by means of a spring 208, which biases the locking button 162 distally, thus the inner surface of locking button 162 applies radial force on and inwardly deflects deformable leaves 210 formed on the outer surface of the distal end of tool handgrip 152 of the endoscopic tool sub-assembly 150. This engagement between the locking button 162 and deformable leaves 210 results in increased friction between handgrip 130 and endoscopic tool subassembly 150, thus axially locking the endoscopic tool 156 with respect to the working channel subassembly 100.

It is additionally seen in FIG. 15A that the hollow shaft 102 is fixedly attached to handgrip 130 of the working shaft subassembly 100. The spine cover 122 is also fixedly attached to handgrip 130 and spine pushrod 120 is fixedly attached to working channel articulating knob 140, having an inner helical groove path 222 (shown particularly in FIGS. 12B & 12C), so that upon rotation of working channel articulating knob 140, the spine pushrod 120 is axially distally displaced due to displacement along inner helical groove path 222. Axial displacement of spine pushrod 120 causes bending of articulating joint 118, and thus bending of hollow shaft 102, and in turn bending of flexible shaft 154 of the endoscopic tool subassembly 150.

It is appreciated that each bending angle of the articulating joint 118 and as a consequence of the hollow shaft 102 and flexible shaft 154 can be temporarily locked by means of rotation of locking knob 142, which locks further rotation of working channel articulating knob 140. The working channel articulating knob 140 is biased to the proximal orientation of spine pushrod 120, in which the articulating joint 118 is not bent, by means of the biasing force of spring 224.

It is particularly seen in FIG. 15B that the articulating joint 118 is in its bent orientation and thus flexible shaft 154 is bent and endoscopic tool 156 extends substantially at an angle with respect to longitudinal axis 155. Additionally, in this operative orientation part of the flexible shaft 154 and the endoscopic tool 156 extend distally from hollow shaft 102 of the working channel subassembly 100.

It is a particular feature of an embodiment of the present invention that the working channel device has various degrees of freedom, such that the working channel device has various degrees of freedom, such that the endoscopic tool subassembly 150 can be manually rotated with respect to the working channel subassembly 100. The entire working channel assembly 170 can be manually rotated within the patient body in order to introduce the endoscopic tool 156 at a different orientation.

It is particularly seen in FIGS. 13-14B that the endoscopic tool subassembly 150 is in a non-rotated operative orientation with respect to working channel subassembly 100, thus endoscopic tool 156 generally lies along a plane which extends transversely with respect to the plane along which the spine 110 extends.

It is appreciated that the articulating joint 118 can be initially positioned at a non-bent orientation and bending of the articulating joint at angles of 0-90° with respect to longitudinal axis 155 is enabled by working channel articulating knob 140. Alternatively, the articulating joint 118 can be initially positioned at angle with respect to longitudinal axis 155, such as −45° and then bending of the articulation joint 118 up to an angle of +45° with respect to longitudinal axis 155 is enabled by working channel articulating knob 140.

It is further appreciated that various endoscopic tools may be repeatedly interchanged within the working channel subassembly 100 during a single procedure. It is appreciated that various tools can be used, such as tools useful for arthroscopy, laparoscopy and other medical applications.

It will be appreciated by persons skilled in the art that the present invention is not limited by what has been particularly shown and described hereinabove. Rather the scope of the present invention includes both combinations and sub-combinations of various features described hereinabove as well as variations and modifications thereof which are not in the prior art.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting. In addition, any priority document(s) of this application is/are hereby incorporated herein by reference in its/their entirety.

What is claimed is:

1. An articulating working channel system for use with at least one flexible tool subassembly which is adapted to be utilized in a single surgical procedure, comprising:
   a working channel subassembly including a flexible shaft having a longitudinal axis and a distal end;

a surgical tool subassembly including a flexible tool, wherein said flexible tool is adapted to be inserted into said flexible shaft; and wherein said working channel subassembly includes a bendable section and has only a single articulatable joint at said working channel subassembly bendable section, said working channel subassembly bendable at said bendable section only at said single articulatable joint, said joint being articulatable between a first position in which said working channel subassembly is positioned at a first angle relative to said longitudinal axis and a second position in which said working channel subassembly is positioned at a second angle relative to said longitudinal axis, said first angle being different from said second angle;

wherein said flexible shaft has a bendable location disposed between first and second unbent portions of said flexible shaft, and wherein said flexible shaft is adapted to be articulated by said single articulatable joint at said working channel subassembly bendable section, and said flexible tool is adapted to be passively articulated with said flexible shaft, at said flexible tool bendable section; and wherein said system includes a spine having a distal end and extending longitudinally along the entire length of said flexible shaft, said spine attached to said flexible shaft at least at said shaft distal end.

2. An articulating working channel system according to claim 1 and wherein said flexible tool is adapted to be axially displaced with respect to said flexible shaft.

3. An articulating working channel system according to claim 1 and wherein said flexible tool is adapted to be rotationally displaced with respect to said flexible shaft.

4. An articulating working channel system according to claim 1 and wherein said working channel subassembly and said surgical tool subassembly are adapted to be operated using a single handle.

5. An articulating working channel system according to claim 1, wherein said articulatable joint is adjacent to a distal portion of said spine.

6. An articulating working channel system according to claim 1, wherein said spine is rigid.

7. An articulating working channel system according to claim 1, wherein said spine is pivotable at said articulatable joint.

8. An articulating working channel system according to claim 1, wherein said flexible shaft is attached to said spine at least at a distal portion of said shaft.

9. An articulating working channel system according to claim 1, wherein said spine includes a distal end and wherein said spine distal end is configured for one of grasping and passing surgical sutures.

10. An articulating working channel system according to claim 1, wherein said system includes an articulatable knob, wherein rotation of said articulatable knob is associated with a corresponding articulating of said articulatable joint.

11. An articulating working channel system according to claim 1, wherein said flexible shaft is extendible.

12. An articulating working channel system according to claim 10, wherein said system includes a pushrod extending distally from said articulatable knob to said articulatable joint, wherein rotation of said articulatable knob is associated with a corresponding axial displacement of said pushrod.

13. An articulating working channel system according to claim 10, wherein said articulatable knob includes an inner helical groove path, wherein rotation of said articulatable knob is associated with a corresponding axial displacement of said pushrod, and said articulation of said flexible shaft.

14. An articulating working channel system according to claim 10, wherein said articulatable knob is biased to a proximal orientation of said pushrod.

15. An articulating working channel system according to claim 1, said system including a locking knob, wherein rotation of said locking knob from a first position to a second position prevents articulating of said articulatable joint.

16. An articulating working channel system according to claim 1, wherein said working channel subassembly has a noncircular cross-sectional profile.

17. An articulating working channel system according to claim 1, wherein said working channel subassembly has an oval-shaped cross-sectional profile.

18. An articulating working channel system according to claim 1, wherein said working channel subassembly has an inner rectangular profile.

19. An articulating working channel system according to claim 1, wherein said working channel subassembly includes at least one partition extending longitudinally along said working channel subassembly, wherein said at least one partition divides said working channel subassembly into a plurality of separate longitudinal channels.

20. An articulating working channel system according to claim 1, wherein said working channel subassembly includes a plurality of longitudinally extending channels.

21. An articulating working channel system according to claim 20, wherein said plurality of longitudinally extending channels extend in a parallel configuration along said working channel subassembly.

22. An articulating working channel system according to claim 20, wherein at least one of said plurality of longitudinally extending channels includes at least one said channel disposed within another one of said channels.

23. An articulating working channel system according to claim 1, wherein said working channel subassembly includes a second flexible shaft attached to said flexible shaft, said second flexible shaft sized and shaped for insertion thereinto of a second flexible tool.

24. An articulating working channel system according to claim 23, wherein said flexible shaft has an outer cross-sectional profile, wherein said articulatable joint is attached to said flexible shaft at a first preselected point along said flexible shaft outer cross-sectional profile, and wherein said second flexible shaft extends parallel to said flexible shaft adjacent a second preselected point along said flexible shaft outer cross-sectional profile, said second preselected point offset 90 degrees along said flexible shaft outer cross-sectional profile from said second preselected point.

25. An articulating working channel system according to claim 23, wherein said flexible shaft has an outer cross-sectional profile, wherein said articulatable joint is attached to said flexible shaft at a first preselected point along said flexible shaft outer cross-sectional profile, and wherein said second flexible shaft extends parallel to said flexible shaft adjacent a second preselected point along said flexible shaft outer cross-sectional profile, said second preselected point offset 180 degrees along said flexible shaft outer cross-sectional profile from said second preselected point.

26. An articulating working channel system according to claim 1, wherein said spine is a continuous rigid spine longitudinally attached along the length of said shaft;

wherein said rigid spine includes said single articulating joint adjacent said working channel bendable section, and wherein bending of said rigid spine at said single articulating joint causes bending of said working channel subassembly bendable section.

27. An articulating working channel system according to claim 1, wherein said working channel subassembly is bendable at said bendable section only at a single axial bending location of said single articulatable joint, said joint being articulatable at said single axial bending location to a position of 90 degrees relative to said longitudinal axis.

28. An articulating working channel system according to claim 1, wherein said working channel subassembly
   wherein said spine includes a proximal portion and wherein said articulatable joint is configured to be actuated by axial movement of said spine proximal portion relative to said flexible shaft.

29. An articulating working channel system according to claim 1, wherein said articulatable joint is positioned adjacent said spine distal end, and wherein said spine is non-bendable along all of its length except at a pivot point along said spine.

\* \* \* \* \*